(12) United States Patent
Johnson et al.

(10) Patent No.: US 7,915,285 B2
(45) Date of Patent: Mar. 29, 2011

(54) METHOD FOR TREATING DRUG AND BEHAVIORAL ADDICTIONS

(75) Inventors: Kirk W. Johnson, Moraga, CA (US); Linda May Rothblum Watkins, Boulder, CO (US)

(73) Assignees: The Regents of the University of Colorado, Denver, CO (US); Medicinova, Inc., San Diego, CA (US)

( * ) Notice: Subject to any disclaimer, the term of this patent is extended or adjusted under 35 U.S.C. 154(b) by 1219 days.

(21) Appl. No.: 11/527,757

(22) Filed: Sep. 26, 2006

(65) Prior Publication Data

US 2007/0072899 A1    Mar. 29, 2007

Related U.S. Application Data

(60) Provisional application No. 60/720,568, filed on Sep. 26, 2005, provisional application No. 60/810,038, filed on May 31, 2006.

(51) Int. Cl.
*A61K 31/4745* (2006.01)
(52) U.S. Cl. ...................................... 514/303
(58) Field of Classification Search .................... 514/303
See application file for complete search history.

(56) References Cited

U.S. PATENT DOCUMENTS

| | | | | |
|---|---|---|---|---|
| 5,496,836 A * | 3/1996 | Di Rocco et al. | ............. | 514/370 |
| 6,828,349 B1 * | 12/2004 | Dewey et al. | ................. | 514/561 |
| 6,953,774 B2 * | 10/2005 | Palmer et al. | ................. | 514/21.1 |
| 2003/0195194 A1 | 10/2003 | Gaeta et al. | | |
| 2006/0008446 A1 | 1/2006 | Watkins | | |
| 2006/0106054 A1 * | 5/2006 | Nagasawa et al. | ............ | 514/303 |
| 2006/0160843 A1 | 7/2006 | Johnson et al. | | |
| 2007/0072899 A1 | 3/2007 | Johnson et al. | | |
| 2007/0281966 A1 | 12/2007 | Johnson et al. | | |
| 2008/0114027 A1 | 5/2008 | Johnson et al. | | |
| 2008/0181876 A1 | 7/2008 | Johnson et al. | | |

FOREIGN PATENT DOCUMENTS

| | | | |
|---|---|---|---|
| CA | 2508194 | * | 6/2004 |
| WO | WO 99/64037 A1 | | 12/1999 |
| WO | WO 01/05422 A2 | | 1/2001 |
| WO | WO 03/104178 A | | 12/2003 |
| WO | WO 03/104203 A | | 12/2003 |
| WO | WO 2004/058713 A | | 7/2004 |
| WO | WO 2005/058304 A | | 6/2005 |
| WO | WO 2006/045505 A | | 5/2006 |
| WO | WO 2006/063048 A2 | | 6/2006 |
| WO | WO 2006/108671 A | | 10/2006 |
| WO | WO 2007/047978 A2 | | 4/2007 |

OTHER PUBLICATIONS

Chihara et al. Inhibitory effect of ibudilast (KC-404) on the expression of the b2 integrin family on an eosinophilic cell line (EoL-1). Annals of Allergy, ASthma, &Immunology, Nov. 1998, vol. 81 pp. 448-450.*

Murashima et al. Inhibitory effect of ibudilast (KC 404) on cyclic nucreotide phosphodiesterases. Janpanese Pharmacology and Therapeutics, 1998 vol. 26, No. 1 pp. 41-45, abstract.*

Gibson, et al., "The Inhibitory Profile of Ibudilast Against the Human Phosphodiesterase Enzyme Family," *Eur J Pharmacology* 538:39-42 (2006).

Gul, et al., "The Interaction Between IL-1B and Morphine: Possible Mechanism of the Deficiency of Morphine-Induced Analgesia in Diabetic Mice," *Pain* 89:39-45 (2000).

Johnston, et al., "A Role for Proinlammatory Cytokines and Fractalkine in Analgesia, Tolerance, and Subsequent Pain Falicitation Induced by Chronic Intrathecal Morphine," *J Neurosci* 24:7353-7365 (2004).

Mizuno, et al.,"Neuroprotective Role of Phosphodiesterase Inhibitor Ibudilast on Neuronal Cell Death Induced by Activated Microglia," *Neuropharmacology* 46:404-411 (2004).

Narita, et al., "Direct Evidence of Astrocytic Modulation in the Development of Rewarding Effects Induced by Drugs of Abuse," *Neuropsychopharmacology* 31:2476-2488 (2006).

Obernolte, et al., (The cDNA of a Human Lymphocyte Cyclic-AMP Phosphodiesterase (PDE IV) Reveals a Multigene Family, Gene 129:239-247 (1993).

Raghavendra, et al., "The Role of Spinal Neuroimmune Activation in Morphine Tolerance/Hyperalgesia in Neuropathic and Sham-Operated Rats," *J Neurosci* 22:9980-9989 (2002).

Raghavendra, et al., "Attenuation of Morphine Tolerance, Withdrawal-Induced Hyperalgesia, and Associated Spinal Inflammatory Immune Responses by Propentofylline in Rats," *Neuropsychopharmacology* 29:327-334 (2004).

Rile, et al., "Potentiation of Ibudilast Inhibition of Platelet Aggregation in the Presence of Endothelial Cells," *Thrombosis Research* 102:239-246 (2001).

Shavit, et al., "Interleukin-1 Antagonizes Morphine Analgesia and Underlies Morphine Tolerance," *Pain* 115:50-59 (2005).

Song, et al., "The Involvement of Glial Cells in the Development of Morphine Tolerance," *Neuro Res* 39:281-286 (2001).

Souness, et al., "Possible Role of Cyclic AMP Phosphodiesterases in the Actions of Ibudilast on Eosinophil Thromboxane Generation and Airways Smooth Muscle Tone," *Br, J Pharmacol* 111:1081-1088 (1994).

Sugiyama, et al., "SPECT Evaluation of Effect of Cerebral Vasodilator by the Subtraction Method Using Tc-99$^m$ HMPAO," *No To Shinkei* 45(2):139-142 (1993) English Abstract.

Suzumura, et al., "Ibudilast Suppresses TNFa Production by Glial Cells Functioning Mainly as Type III Phosphodiesterase nhibitor in the CNS," *Brain Res* 837:203-212 (1999).

Takuma, et al., "Ibudilast Attenuates Astrocyte Apoptosis Via Cyclic GMP Signalling Pathway in an In Vitro Reperfusion Model," *British Journal of Pharmacology* 133:841-848 (2001).

Wakita, et al., "Ibudilast, a Phosphodiesterase Inhibitor, Protects Against White Matter Damage Under Chronic Cerebral Hyperfusion in the Rat," *Brain Res* 992:53-59 (2003).

(Continued)

*Primary Examiner* — Jennifer M Kim
(74) *Attorney, Agent, or Firm* — Gilberto M. Villacorta; Malcolm J. Kavarana; Foley & Lardner LLP

(57) ABSTRACT

The present invention is directed to the use of ibudilast for treating addictions, including drug and behavioral addictions. In particular, ibudilast is used to diminish the dopamine-mediated reward associated with addictions and to treat withdrawal syndromes after discontinuance of addictive drug use or behavior.

53 Claims, 11 Drawing Sheets

OTHER PUBLICATIONS

Watkins and Maier, "Beyond Neurons: Evidence That Immune and Glial Cells Contribute to Pathological Pain States," *Physiol Rev* 82:981-1011 (2002).

Watkins and Maier, "Targeting Glia to Control Clinical Pain: An Idea Whose Time has Come," *Drug Disc Today* 1(1):83-88 (2004).

Watkins, et al., "Glia: Novel Counter-Regulators of Opoid Analgesia," *Trends Neurosci* 28(12):661-669 (2005).

Bloom & Bennett, "Mechanism of a reaction in vitro associated with delayed-type hypersensitivity," *Science* 153:80-82 (1966).

Calandra & Roger, "Macrophage migration inhibitory factor: a regulator of innate immunity," *Nat Rev Immunol* 3:791-800 (2003).

Calandra, et al., "Protection from septic shock by neutralization of macrophage migration inhibitory factor," *Nat Med* 6:164-170 (2000).

Feng, et al., "Ibudilast, A Nonselective Phosphodiesterase Inhibitor, Regulates Th1/Th2 Balance and NKT Cell Subset in Multiple Sclerosis," *Mult Scler* 10:494-498 (2004).

Fujimoto, et al., "Ibudilast, A Phosphodiesterase Inhibitor, Ameliorates Experimental Autoimmune Encephalomyelitis in Dark August Rat," *J Neuroimmunology* 95:35-42 (1999).

Kawanokuchi, et al., "Effects of Interferon-Beta On Microglial Functions As Inflammatory and Antigen Presenting Cells in the Central Nervous System," *Neuropharmacology* 46:734-742 (2004).

Koda, et al., "Up-Regulation of Macrophage Migration-Inhibitory Factor Expression After Compression-Induced Spinal Cord Injury in Rats," *Acta Neuropathol* 108:31-36 (2004).

Narita, et al., "Role of Astrocytes in Rewarding Effects of Drugs Of Abuse," *Jpn J Neuropsychopharmacol* 26:33-39 (2006) *English Abstract*.

Narita, et al., "Comparatice Pharmacological Profiles of Morphine and Oxycodone Under a Neuropathic Pain-Like State in Mice: Evidence for Less Sensitivity to Morphine," *Nature Neuropsychopharmacolog* 1-16 (2007) *Online Article*.

Santos & Morand, "The Role of Macrophage Migration Inhibitory Factor In The Inflammatory Immune Response And Rheumatoid Arthritis," *Wein Med Wochenschr* 156:11-18 (2006).

Futaki, "Treatment of Meniere's Disease Comparison of Prednisolone and Ketas," *Practica Otologica Kyoto* 83(9):1463-1471 (1990) *English Abstract*.

Itoh, et al, "A Therapeutic Strategy to Prevent Morphine Dependence and Tolerance by Coadministration of cAMP-Related Reagents with Morphine," *Methods and Findings in Experimental and Clinical Pharmacology* 20(7):619-625 (1998).

Mamiya, et al., "Involvement of Cyclic AMP Systems in Morphine Physical Dependence in Mice: Prevention of Development of Morphine Depende by Rolipram, A Phosphodiesterase 4 Inhibitor," *Br J Pharmacol* 132(5):1111-1117 (2001).

Nabeshima, et al., "Drug Dependence Formation Inhibitor: Comprising Phosphdoesterase Inhibitor, Preferably Rolipram, Especially for Combatting Narcotic Analgesic Dependence," Database WPI, Derwent Publications, Ltd., London, GB, p. 7, AN 1997-506303 (1997).

Tsuru, et al., "Preference Test of 3-Isobutyryl-2-Isopopylpyrazolo [1,56-a] Pyridine (KC-404) On Rats," *Pharmacometrics* 36(6):449-457 1988 *English Abstract*.

Kudo, et al., "General Pharmacological Activity of KC-404—Effect on Central Nervous System," *Kiso to Rinsho* 19(11):5476-5484 (1985) *Original Japanese Article With Attached Certified English Translation*.

Hutchinson, et al., "Opoid-Induced Glial Activation: Mechanisms of Activation and Implications for Opoid Analgesia, Dependence, and Reward," *Sci World J* 7(S2):98-111 (2007).

Park, et at, "The Effects of Ibudilast On Diabetic Peripheral Neuropathy," *Jpn Pharmacol Ther* 19(5):337-341 (1991) *English Translation, Original Japanese Article, And English Abstrac*.

Park, "The Effects of Ibudilast on Diabetic Peripheral Neuropathy, Part 2" *Jpn Pharmacol Ther* 23(6):133-139 (1995) *English Translation, Original Japanese Article, And English Abstract*.

Shimomura, et al., "Analgesic Induced Headaches: Succesful Treatment With Ibudilast," *Geriatr Med* 29(2):315-323 (1991) *Original Japanese Only*.

Shimomura, et al., "Analgesic-Induced Headaches: Succesful Treatment With Ibudilast," *Headache* 31:483 (1991).

Souness, et al., "Potential of Phosphodiesterase Type 4 Inhibitors in the Treatment of Rheumatoid Arthritis," *Curr Res Rheum Arthritis* 2(6):255-268 (1998).

Yamauchi, "Effects of Ibudilast on Diabetic Neuropathy. Subjective and Objective Improvement by Ibudilast," *Clin Res* 71(9):262-272 (1994) *English Translation and Original Japanese Article*.

Yasaki, et al., "Effect of Ibudilast on Experimental Diabetic Neuropathy," *J Japan Diab Soc* 37(3):215-222 (1994) *English Translation, Original Japanese Article, And English Abstract*.

Bender, et al., "Cyclic Nucleotide Phosphodiesterases: Molecular Regulation to Clinical Use," *Pharmacol Rev* 58:488-520 (2006).

Castro, et al., "Cyclic Nucleotide Phosphodiesterases And Their Role in Immunomodulatory Responses: Advances in the Development of Specific Phosphdiesterase Inhibitors," *Medicinal Res Rev* 25(2):229-244 (2005).

He, et al., "Novel Cyclic Compounds As Potent Phosphdiesterase 4 Inhibitors," *J Med Chem* 41:4216-4223 (1998).

Huang, et al., "Preferential Inhibition of Human Phosphodiesterase 4 By Ibudilast," *Life Sci* 78:2663-2668 (2006).

Johnson, et al., "72 AV411: A Unique, Orally Active Glial Inhibitor for Neuropathic Pain," *Eur J Pain* 10(1):S21 (2006).

Kiritsy-Roy, et al., "Dopamine D-1 And D-2 Receptor Antagonists Potentiate Analgesic and Motor Effects of Morphine," *Pharmacol Biochem Behav* 32:717-721 (1989).

Ledeboer, et al., "Ibudilast (AV-411). A New Class Therapeutic Candidate for Neuropathic Pain And Opoid Withdrawal Syndromes," *Exp Opin Invest Drugs* 16(7):935-950 (2007).

Miguel-Hidalgo, "Withdrawal From Free-Choice Ethanol Consumption Results in Increased Packing Density Of Glutamine Synthetase-Immunoreactive Astrocytes in the Prelimbic Cortex of Alcohol-Preferring Rats," *Alcohol* 41:379-385 (2006).

Tsuneichi, et al., "Effect of Continous Oral Administration of KC-764 on Monoamines, Acetylcholine and Neuroactive Amino Acids Contents in Rat Brain," *Clinical Rep* 28(8):113-119 (1994) *Original Japanese Article and English Abstract*.

\* cited by examiner

METHOD FOR TREATING DRUG AND BEHAVIORAL ADDICTIONS

CROSS-REFERENCE TO RELATED APPLICATION

This application claims benefit under 35 U.S.C. §119(e) of provisional application 60/720,568, filed Sep. 26, 2005, and provisional application 60/810,038, filed May 31, 2006, which applications are hereby incorporated by reference in their entireties.

STATEMENT REGARDING FEDERALLY SPONSORED RESEARCH OR DEVELOPMENT

This invention was made with support under NIH Grants DA017670 and DA015642, from the National Institute of Drug Abuse. Accordingly, the United States Government may have certain rights in this invention.

FIELD OF THE INVENTION

The present invention relates generally to methods for treating drug and behavioral addictions. In particular, the present invention pertains to methods for treating addictions, such as opiate dependence, with ibudilast (also termed AV411 herein) in order to suppress the release of dopamine in the nucleus accumbens, which is associated with the sense of reward subjects experience in response to addictive drugs and behavior. Additionally, ibudilast can be used for treating withdrawal syndromes after discontinuance of addictive drug use or behavior. Ibudilast is specifically shown to relieve opiate withdrawal symptoms and to attenuate opiate-induced brain glial cell activation which may be linked to opiate tolerance and withdrawal phenomena.

BACKGROUND OF THE INVENTION

The addictiveness of certain drugs and compulsive behaviors is linked to excitation of dopamine mediated reinforcement/reward pathways in the central nervous system (Abbott (2002) Nature 419:872-874; Montague et al. (2004) Nature 431:760-767). Normally dopamine functions to motivate mammals to perform behaviors important for survival, such as eating and sex, but in subjects with addictions, dopamine induces maladaptive behavior. Subjects with addictions feel compelled to use a substance or perform a behavior repeatedly despite experiencing harmful effects. Virtually all drugs of abuse and compulsive behaviors have been shown to increase extracellular dopamine concentrations in the nucleus accumbens of mammals.

Drugs of abuse induce dopamine-mediated dependence characterized by compulsive drug craving and drug seeking behaviors. The World Health Organization (WHO) has classified addictive drugs into nine groups: 1. alcohol, 2. amphetamines, 3. barbiturates, 4. marijuana, 5. cocaine, 6. hallucinogens, 7. khat, 8. opiates, and 9. organic solvents. Dysregulation of dopamine pathways is also associated with compulsive behavioral addictions, such as excessive eating, drinking, smoking, shopping, gambling, sex, and computer use (Comings et al. (2000) Prog. Brain Res. 126:325-341; Comings et al. (1997) 2:44-56; Blum et al. (2000) J. Psychoactive Drugs 32 suppl:i-iv, 1-112; Potenza (2001) Semin. Clin. Neuropsychiatry 6:217-226; Gianoulakis (1998) Alcohol Health Res. World 22:202-210; Bowirrat et al. (2005) Am. J. Med. Genet. B Neuropsychiatr. Genet. 132:29-37; Di Chiara (2005) Physiol. Behav. 86:9-10; Franken et al. (2005) Appetite 45:198-201; Wang et al. (2004) J. Addict Dis. 23:39-53; Aamodt (1998) Nature Med. 4:660; and Koepp et al. (1998) Nature 393:266-268).

In addition, physical and psychological dependence accompanied by withdrawal syndrome is often associated with use of addictive drugs and compulsive behavior. Withdrawal is defined as the appearance of physical and behavioral symptoms upon reduction or cessation of drug use or compulsive behavior. Withdrawal reflects changes occurring in the central nervous system in response to continued use of a substance or repetition of addictive behavior that usurp the normal mechanisms mediating reinforcement and reward of behavior to motivate the addicted individual to continue consuming a drug or repeating compulsive behavior in the face of serious social, legal, physical and professional consequences. Physical symptoms of withdrawal may include intense cravings, irritability, anxiety, dysphoria, restlessness, lack of concentration, lightheadedness, insomnia, tremor, increased hunger and weight gain, yawning, perspiration, lacrimation, rhinorrhoea, dilated pupils, aching of bones, back and muscles, piloerection, hot and cold flashes, nausea, vomiting, diarrhea, weight loss, fever, and increased blood pressure, pulse and respiratory rate.

The management of opioid withdrawal syndrome has long been recognized as an unmet clinical need. Chronic pain afflicts upwards of one in three adults worldwide. Opioid compounds, such as morphine, are frontline therapeutics for the control of chronic pain. Because chronic pain, by definition, persists for many months (and up to the remainder of the patient's life), morphine and like compounds may be given chronically as well. This is a dire problem because opioids induce dependence upon repeated administration, meaning that continuing administration of opioids is required for patients to function normally. When opioids are discontinued, and also during the temporal lag between successive doses of opioids, the patient goes into withdrawal.

Because opioids exert actions in a wide array of brain, spinal cord and bodily tissues, the effects of opioids, and consequent withdrawal symptomologies, are diverse. The signs of withdrawal are generally opposite to the effects of opioids. For example, morphine causes constipation; withdrawal causes diarrhea. Morphine decreases core body temperature, withdrawal raises it. Morphine causes sedation, withdrawal causes agitation. Additional signs of withdrawal include increased pain, dilated pupils, goose pimples, yawning, cramps, muscle aches, restlessness, extreme anxiety, insomnia, nausea and vomiting, sweating, tearing, tachycardia, and increased blood pressure.

Perversely, although pain reduction is the reason that opioids are administered, pain dramatically rebounds during withdrawal such that pain is not only not controlled by the opioids in the area of the original pain complaint, but rather the entire body is now extraordinarily sensitive to touch and temperature stimuli, misinterpreting ordinarily nonpainful stimuli as painful. Light touch becomes painful. Warm and cool become painful. This twist of everyday sensation into threatening pain (along with the other withdrawal symptomology) destroys, on a daily basis, the lives of many millions in the U.S. alone. It creates great suffering in chronic opioid recipients, in patients needing to discontinue opioids, and in recovering drug addicts, whose desire to avoid withdrawal symptoms may prevent them from escaping from illicit drug use.

The problem is compounded by the fact that there is currently no remedy for withdrawal, short of another dose of opioid. As addicts know, another dose of the drug does nothing to solve the problem but instead only masks the problem until the drug yet again wears off. Current approaches to bringing patients and addicts through withdrawal are dire, including "cold turkey", sedation, and analgesia. "Detoxification" is often induced with naltrexone (an opioid receptor antagonist) under general anaesthesia or benzodiazepine sedation, in a closely monitored environment such as intensive care. Naltrexone induces acute withdrawal, with symptoms that last for about six days. It is only considered for patients in good health. Other currently employed methods to take humans through withdrawal include administration of non-steroidal anti-inflammatory drugs such as paracetamol, anti-emetics such as metoclopramide, anti-diarrheals such as loperamide, diazepam to reduce anxiety and agitation, and clonidine to decrease anxiety, sweating, and changes in heart rate and blood pressure.

In developing an improved treatment for opioid withdrawal it is important to consider that opioids, including morphine, do not just affect neurons. While opioid-responsive neurons in various brain and spinal cord regions suppress pain, lower core body temperature, alter hormone release, etc. (the classical effects of opioids), it has recently been discovered that opioids also affect a non-neuronal cell type called glia (microglia, astrocytes, oligodendrocytes). Morphine and other opioids activate glia. This activation increases with repeated opioid administration, as evidenced by the upregulation of glia-specific activation markers. That such glial activation contributes to morphine tolerance is supported by the finding that co-administering glial inhibitors along with morphine disrupts the development of morphine tolerance. It follows that reduction of glial activation may be useful as a therapeutic approach to disrupting the development of morphine tolerance. Watkins, L. R. et al. (2005) *Trends in Neuroscience* 28:661-669; Gul, H. et al. (2000) *Pain* 89:39-45; Johnston, I. N. et al. (2004) *J Neurosci.* 24:7353-65; Raghavendra, V. et al. (2002) *J Neurosci* 22 (22):9980-89; Raghavendra, V. et al. (2004) *Neuropsychopharmacology* 29 (2):327-34; Shavit, Y. et al. (2005) *Pain* 115:50-59; Song, P. and Zhao, Z. Q. (2001) *Neurosci. Res.* 39:281-86.

Opioid-driven progressive glial activation causes glia to release neuroexcitatory substances, including the proinflammatory cytokines interleukin-1 (IL-1), tumor necrosis factor (TNF), and interleukin-6 (IL-6). These neuroexcitatory substances counteract the pain-relieving actions of opioids, such as morphine, and drive withdrawal symptomology, as demonstrated by experiments involving co-administration or pro- or anti-inflammatory substances along with morphine. For example, injecting IL-1 into the cerebrospinal fluid of mice at a dose having no behavioral effect on its own blocks the analgesic effect of systemic morphine. Similarly, spinal delivery of morphine and IL-1 receptor antagonist (which prevents IL-1 from exerting its effects), or morphine and the anti-inflammatory cytokine IL-10 (which downregulates the production, release and efficacy of proinflammatory cytokines), enhances the magnitude and duration of morphine analgesia. Indeed, if morphine analgesia is established and then allowed to dissipate, potent analgesia can be rapidly reinstated by injecting IL-1 receptor antagonist, suggesting that dissipation of analgesia is caused by the activities of pain-enhancing proinflammatory cytokines rather than dissipation of morphine's analgesic effects.

The activity of other opioids may also be opposed by activation of glia. Studies show that glia and proinflammatory cytokines compromise the analgesic effects of methadone, at least in part, via non-classical opioid receptors (Watkins, L. R. et al. (2005) *Trends Neurosci.* 28:661-669). These results suggest that glia and proinflammatory cytokines will be involved in methadone withdrawal, and likely withdrawal from other opioids as well. These data also expand the clinical implications of glial activation, since cross-tolerance between opioids may be explained by the activation of the glial pain facilitatory system, which undermines all attempts to treat chronic pain with opioids.

In summary, opioids excite glia, which in turn release neuroexcitatory substances (such as proinflammatory cytokines) that oppose the effects of opioids and create withdrawal symptoms upon cessation of opioid treatment. Compounds that suppress such glial activation would be beneficial novel therapeutics for treatment of opioid withdrawal.

There remains a need for improved compounds, compositions, and methods of treatment for drug and behavioral addictions. In particular, drugs are needed that attenuate or abolish the dopamine mediated "reward" associated with addicts' cravings and that alleviate symptoms of withdrawal syndromes after discontinuance of drug use or compulsive behavior.

SUMMARY OF THE INVENTION

In one aspect, the invention provides a method for suppressing the release of dopamine in the nucleus accumbens of a subject comprising administering to the subject an effective amount of ibudilast.

In certain embodiments, the subject has an addiction. In certain embodiments, the addiction is a drug addiction, for example, an opiate, cocaine, amphetamine, methamphetamine, cannabinoid, alcohol, or nicotine addiction. In other embodiments, the addiction is a behavioral addiction, for example, an eating, drinking, smoking, shopping, gambling, sex, or computer use addiction.

In certain embodiments, the subject is a human. In certain embodiments, ibudilast is administered systemically, for example, via intravenous, subcutaneous, oral, intranasal, sublingual or other systemic routes. In other embodiments, ibudilast is administered centrally, for example, intrathecally. In certain embodiments, multiple therapeutically effective doses of ibudilast are administered to the subject. In certain embodiments, ibudilast is administered according to a daily dosing regimen. In certain embodiments ibudilast is administered twice a day. In certain embodiments, ibudilast is administered intermittently.

In another aspect, the invention provides a method for treating an addiction comprising administering to a subject in need thereof a therapeutically effective amount of ibudilast.

In certain embodiments, the invention provides a method for diminishing or eliminating addiction-related behavior of a subject.

In certain embodiments, the invention provides a method for diminishing or eliminating cravings associated with addiction to a drug in a subject.

In certain embodiments, the invention provides a method for diminishing or eliminating tolerance to a drug in a subject.

In certain embodiments, the invention provides a method for diminishing or eliminating the incentive salience of drug—or addictive behavior—associated cues in a subject.

In certain embodiments, the invention provides a method for diminishing or eliminating symptoms of withdrawal syndrome in a subject.

In certain embodiments, the invention provides a method for diminishing or eliminating weight loss in a subject.

In certain embodiments, the invention provides a method for diminishing or eliminating glial cell activation in a subject. In certain embodiments, microglia activation is diminished or eliminated in the subject. In certain embodiments, astrocyte activation is diminished or eliminated in the subject. In certain embodiments, drug-induced increases of CD11b are reduced in the brain of the subject, for example, in the periaqueductal grey or trigeminal nucleus regions of the brain of the subject.

In certain embodiments, the invention provides a method for diminishing or eliminating drug-induced increases in proinflammatory cytokine expression in a subject. In certain embodiments, the proinflammatory cytokine is interleukin-1. In certain embodiments, proinflammatory cytokine expression is reduced in the brain of the subject. In certain embodiments, interleukin-1 expression is reduced in the dorsal periaqueductal grey region of the brain of the subject.

In certain embodiments, the subject is a human. In certain embodiments, ibudilast is administered systemically, for example, via intravenous, subcutaneous, oral, intranasal, sublingual or other systemic routes. In other embodiments, ibudilast is administered centrally, for example, intrathecally. In certain embodiments, multiple therapeutically effective doses of ibudilast are administered to the subject. In certain embodiments, ibudilast is administered according to a daily dosing regimen. In certain embodiments ibudilast is administered twice a day. In certain embodiments, ibudilast is administered intermittently.

In certain embodiments, the addiction is a drug addiction, for example, an opiate, cocaine, amphetamine, methamphetamine, cannabinoid, alcohol, or nicotine addiction. In other embodiments, the addiction is a behavioral addiction, for example, an eating, drinking, smoking, shopping, gambling, sex, or computer use addiction.

In certain embodiments, ibudilast is used in combination therapy with one or more other agents for treating an addiction. In some embodiments, one or more agents are selected from the group consisting of analgesics, non-steroidal anti-inflammatory drugs (NSAIDs), antiemetics, antidiarrheals, alpha-2-antagonists, benzodiazepines, anticonvulsants, antidepressants, and insomnia therapeutics. In various embodiments, one or more agents are selected from the group consisting of buprenorphine, naloxone, methadone, levomethadyl acetate, L-alpha acetylmethadol (LAAM), hydroxyzine, diphenoxylate, atropine, chlordiazepoxide, carbamazepine, mianserin, benzodiazepine, phenoziazine, disulfiram, acamprosate, topiramate, ondansetron, sertraline, bupropion, amantadine, amiloride, isradipine, tiagabine, baclofen, propranolol, desipramine, carbamazepine, valproate, lamotrigine, doxepin, fluoxetine, imipramine, moclobemide, nortriptyline, paroxetine, sertraline, tryptophan, venlafaxine, trazodone, quetiapine, zolpidem, zopiclone, zaleplon, gabapentin, naltrexone, paracetamol, metoclopramide, loperamide, clonidine, lofexidine, and diazepam.

In another aspect, the invention relates to methods of treating an opioid withdrawal syndrome in a mammalian subject by administering one or more doses of ibudilast. In one embodiment the subject is a human.

In another embodiment the opioid is selected from the group consisting of morphine, methadone, and fentanyl. In one embodiment the opioid is morphine. In some embodiments the opioid withdrawal syndrome is caused by reduction or cessation of administration of an opioid in a subject. In another embodiment the opioid withdrawal syndrome is caused by administration of an opioid antagonist, such as naloxone or naltrexone.

In one embodiment, ibudilast is administered systemically, e.g. via intravenous, subcutaneous, oral, intranasal, sublingual or other systemic routes. In another embodiment, ibudilast is administered centrally, e.g. intrathecally.

In other embodiments, ibudilast is used in combination therapy with one or more other agents for treatment of opioid withdrawal. In some embodiments, one or more agents are selected from the group consisting of analgesics, NSAIDs, antiemetics, antidiarrheals, alpha-2-antagonists, and benzodiazepines. In various embodiments, one or more agents are selected from the group consisting of naltrexone, paracetamol, metoclopramide, loperamide, clonidine, lofexidine, and diazepam.

These and other embodiments of the subject invention will readily occur to those of skill in the art in view of the disclosure herein.

BRIEF DESCRIPTION OF THE FIGURES

FIG. 6A shows a brain sample from an animal treated with vehicle and morphine. FIG. 6B shows a brain sample from a naive animal. FIG. 6C shows a brain sample from an animal treated with ibudilast and morphine. Morphine caused significant microglial activation in the periaqueductal grey region as indicated by CD11b staining (FIG. 6A). Treatment with ibudilast dramatically reduced the increase in the CD11b marker caused by chronic morphine administration (FIG. 6C).

DETAILED DESCRIPTION OF THE INVENTION

Figure 1:
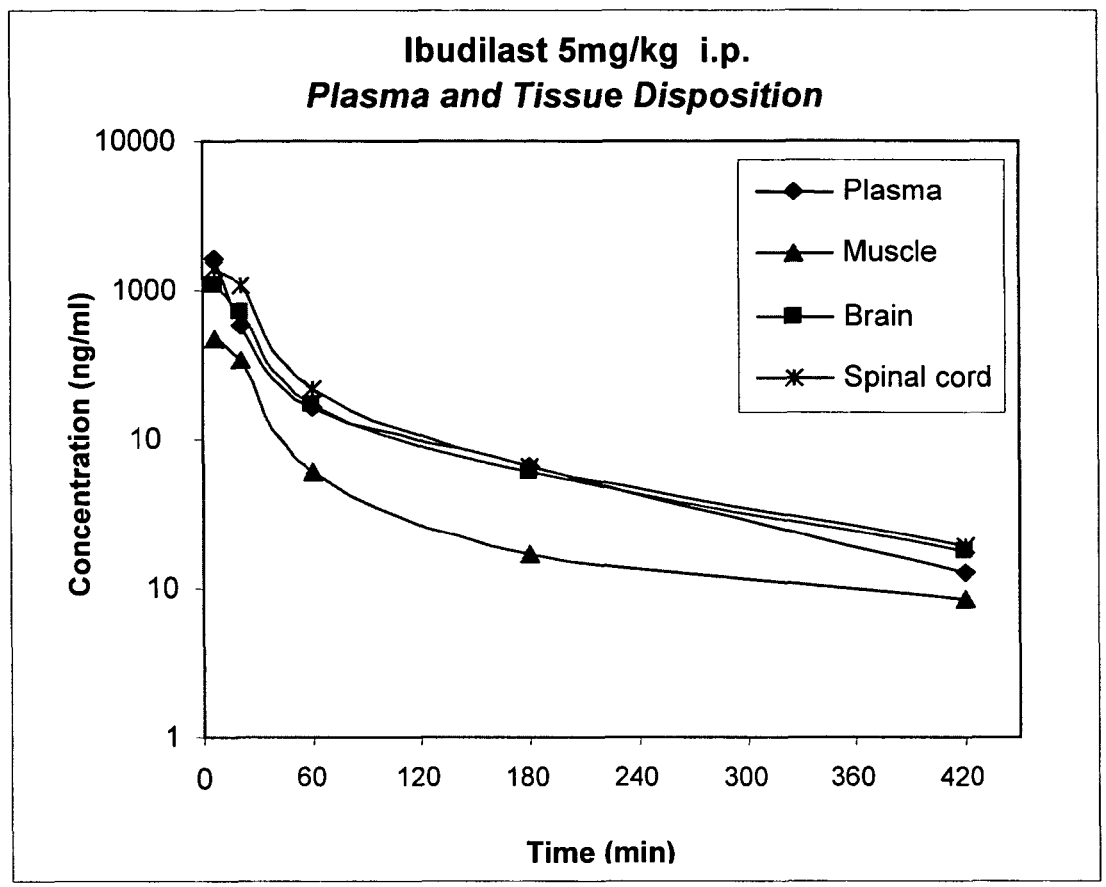
FIG. 1 presents pharmacokinetics and tissue distribution for ibudilast in rats.

The practice of the present invention will employ, unless otherwise indicated, conventional methods of chemistry, biochemistry, and pharmacology, within the skill of the art. Such techniques are explained fully in the literature. See, e.g.; A. L. Lehninger, *Biochemistry* (Worth Publishers, Inc., current addition); Morrison and Boyd, *Organic Chemistry* (Allyn and Bacon, Inc., current addition); J. March, *Advanced Organic Chemistry* (McGraw Hill, current addition); *Remington: The Science and Practice of Pharmacy*, A. Gennaro, Ed., 20$^{th}$ Ed.; *Goodman & Gilman The Pharmacological Basis of Therapeutics*, J. Griffith Hardman, L. L. Limbird, A. Gilman, 10$^{th}$ Ed.

All publications, patents and patent applications cited herein, whether supra or infra, are hereby incorporated by reference in their entirety.

I. Definitions

In describing and claiming the present invention, the following terminology will be used in accordance with the definitions described below.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, hydrobromide, and nitrate salts, or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, the terms further include any physiologically or pharmacologically active substance that produces a localized or systemic effect in a patient.

"Substantially" or "essentially" means nearly totally or completely, for instance, 95% or greater of some given quantity.

"Optional" or "optionally" means that the subsequently described circumstance may or may not occur, so that the description includes instances where the circumstance occurs and instances where it does not.

The term "central nervous system" or "CNS" includes all cells and tissue of the brain and spinal cord of a vertebrate. Thus, the term includes, but is not limited to, neuronal cells, glial cells (astrocytes, microglia, oligodendrocytes), cerebrospinal fluid (CSF), interstitial spaces and the like.

The terms "subject", "individual" or "patient" are used interchangeably herein and refer to a vertebrate, preferably a mammal. Mammals include, but are not limited to, murines, rodents, simians, humans, farm animals, sport animals and pets.

The term "about", particularly in reference to a given quantity, is meant to encompass deviations of plus or minus five percent.

The term "addiction" is defined herein as compulsively using a drug or performing a behavior repeatedly that increases extracellular dopamine concentrations in the nucleus accumbens. An addiction may be to a drug including, but not limited to, psychostimulants, narcotic analgesics, alcohols and addictive alkaloids such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, such as barbiturates, chlordiazepoxide, and alcohols, such as ethanol, methanol, and isopropyl alcohol. The term addiction also includes behavioral addictions, for example, compulsive eating, drinking, smoking, shopping, gambling, sex, and computer use.

A subject suffering from an addiction experiences addiction-related behavior, cravings to use a substance in the case of a drug addiction or overwhelming urges to repeat a behavior in the case of a behavioral addiction, the inability to stop drug use or compulsive behavior in spite of undesired consequences (e.g., negative impacts on health, personal relationships, and finances, unemployment, or imprisonment), reward/incentive effects associated with dopamine release, salience of drug- or behavior-associated cues, dependency, tolerance, or any combination thereof.

Addiction-related behavior in reference to a drug addiction includes behavior resulting from compulsive use of a drug characterized by dependency on the substance. Symptomatic of the behavior is (i) overwhelming involvement with the use of the drug, (ii) the securing of its supply, and (iii) a high probability of relapse after withdrawal.

The terms "effective amount" or "pharmaceutically effective amount" of a composition or agent, as provided herein, refer to a nontoxic but sufficient amount of the composition to provide the desired response, such as suppression of the release of dopamine in the nucleus accumbens of a subject or suppression of glial activation in a subject, and optionally, a corresponding therapeutic effect. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation.

By "therapeutically effective dose or amount" of ibudilast is intended an amount that, when ibudilast is administered as described herein, brings about a positive therapeutic response in treatment of a drug or behavioral addiction, such as diminishing or eliminating addiction-related behavior of a subject, diminishing or eliminating cravings associated with addiction to a drug or a behavior in a subject, diminishing or eliminating tolerance to a drug in a subject, diminishing or eliminating the incentive salience of drug- or behavior-associated cues in a subject, and/or diminishing or eliminating symptoms of withdrawal caused by reduction or cessation of addictive drug use or behavior by a subject.

II. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of a novel therapeutic methodology for safely and effectively treating addiction with ibudilast. The methods of the invention reduce the release of dopamine in the nucleus accumbens, which is associated with cravings and compulsive behavior in addicts. The methods of the invention are particularly useful in diminishing or eliminating addiction-related behavior and alleviating symptoms of withdrawal syndromes in a subject.

In order to further an understanding of the invention, a more detailed discussion is provided below regarding methods of treating addictions with ibudilast.

Treatment of Addictions with Ibudilast

Dopamine release in the nucleus accumbens is thought to mediate the "reward" motivating drug use and compulsive behavior associated with addictions. In one aspect, the invention provides a method for suppressing the release of dopamine in the nucleus accumbens of a subject comprising administering to the subject a composition comprising an effective amount of ibudilast.

Ibudilast has been shown in the present application to suppress the release of dopamine in the nucleus accumbens. As shown in Example 3, ibudilast suppresses dopamine release in the nucleus accumbens in rats treated with morphine, as measured by in vivo microdialysis. In addition, ibudilast suppresses naloxone-induced behavioral signs of morphine withdrawal in rats.

Thus, the invention relates to the use of ibudilast to treat addictions, and in particular, to the use of ibudilast to attenuate or abolish the dopamine mediated "reward" associated with addictions, thus diminishing or eliminating cravings associated with addictions and the accompanying addiction-related behavior and withdrawal syndromes of a subject.

In certain embodiments, a therapeutically effective amount of ibudilast can be administered to a subject to treat a drug addiction. The subject can be addicted to one or more drugs including, but not limited to, psychostimulants, narcotic analgesics, alcohols and addictive alkaloids, such as nicotine, cannabinoids, or combinations thereof. Exemplary psychostimulants include, but are not limited to, amphetamine, dextroamphetamine, methamphetamine, phenmetrazine, diethylpropion, methylphenidate, cocaine, phencyclidine, methylenedioxymethamphetamine and pharmaceutically acceptable salts thereof. Exemplary narcotic analgesics include, but are not limited to, alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. Addictive drugs also include central nervous system depressants, including, but not limited to, barbiturates, chlordiazepoxide, and alcohols, such as ethanol, methanol, and isopropyl alcohol.

In other embodiments, a therapeutically effective amount of ibudilast can be administered to a subject to treat a behavioral addiction. A behavioral addiction can include, but is not limited to, compulsive eating, drinking, smoking, shopping, gambling, sex, and computer use.

In certain embodiments, ibudilast is used in combination therapy with one or more other agents for treating an addiction. Such agents include, but are not limited to, analgesics, NSAIDs, antiemetics, antidiarrheals, alpha-2-antagonists, benzodiazepines, anticonvulsants, antidepressants, and insomnia therapeutics. Exemplary agents include, but are not limited to, buprenorphine, naloxone, methadone, levomethadyl acetate, L-alpha acetylmethadol (LAAM), hydroxyzine, diphenoxylate, atropine, chlordiazepoxide, carbamazepine, mianserin, benzodiazepine, phenoziazine, disulfiram, acamprosate, topiramate, ondansetron, sertraline, bupropion, amantadine, amiloride, isradipine, tiagabine, baclofen, propranolol, desipramine, carbamazepine, valproate, lamotrigine, doxepin, fluoxetine, imipramine, moclobemide, nortriptyline, paroxetine, sertraline, tryptophan, venlafaxine, trazodone, quetiapine, zolpidem, zopiclone, zaleplon, gabapentin, naltrexone, paracetamol, metoclopramide, loperamide, clonidine, lofexidine, and diazepam.

Treatment of Opiate Withdrawal with Ibudilast

The present invention also relates to novel anti-inflammatory approaches to treating opioid dependence and withdrawal, and specifically the use of ibudilast as an effective therapeutic treatment for morphine withdrawal. The clinical manifestations of morphine withdrawal are thought to result, in part, from glial activation in the central nervous system (Narita et al. (2006) *Nature Neuropsychopharmacology* 1-13). Ibudilast is an anti-inflammatory drug with the ability to down-regulate glial cell activation. Mizuno et al. (2004) *Neuropharmacology* 46: 404-411; Suzumura et al. (1999) *Brain Res.* 837:203-212; Wakita et al. (2003) *Brain Res.* 992: 53-59. Systemic (e.g. oral) or central (e.g. intrathecal) administration of ibudilast provides a novel approach to attenuate morphine withdrawal, thereby providing an effective treatment for a condition with few good therapeutic options.

Ibudilast acts to suppress inflammation via action on inflammatory cells (e.g. glial cells) resulting in the suppression of both pro-inflammatory mediator and neuroactive mediator release. While ibudilast (administered systemically) has been extensively explored in several other clinical indications, it has not previously been proposed for relief of morphine withdrawal.

A growing body of literature suggests that repetitive morphine treatment may result in glial cell (microglia, astrocytes) activation, and that such activation may contribute to the sequelae of events associated with morphine tolerance and withdrawal.

Several cues activate glia: immune challenges, infection and/or peripheral inflammation, substances released during prolonged neuron-to-neuron transmission (e.g., neurotransmitters, nitric oxide, prostaglandins, substance P, fractalkine, etc.), neuronal damage (e.g., fractalkine, heat shock proteins, cell wall components), etc. Glial function is changed dramatically upon activation, resulting in elevated release of neuroactive substances. Such events are thought to contribute to altered neurological function with manifestations ranging from neurodegeneration, to pain facilitation, to sensitization of morphine dependence and subsequent withdrawal syndrome. Watkins and Maier (2002) *Physiol. Rev.* 82: 981-1011; Watkins and Maier (2004) *Drug Disc. Today: Ther. Strategies* 1(1): 83-88, etc.

Figure 2:
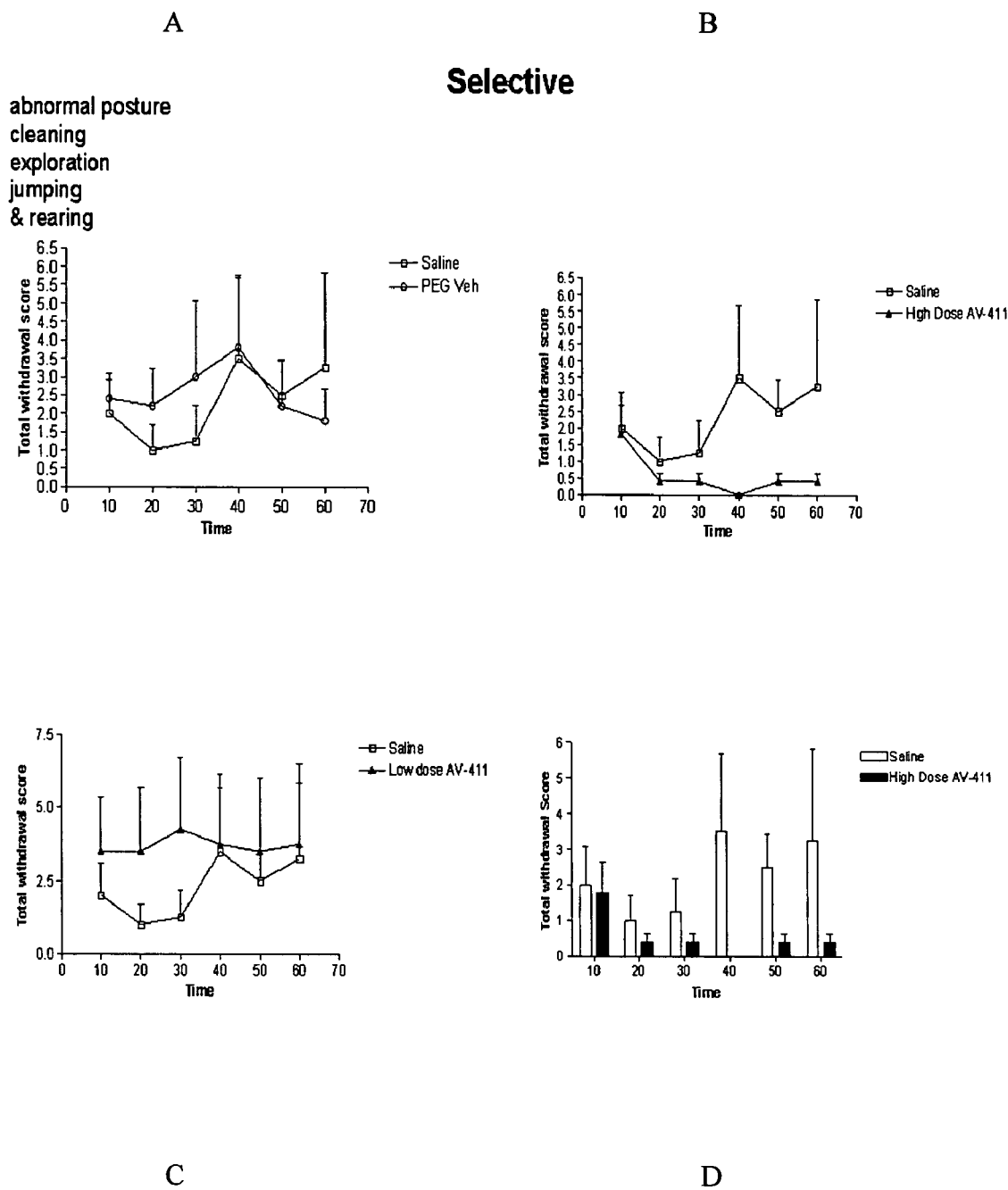
FIGS. 2A, 2B, 2C and 2D are time courses (in minutes) of withdrawal symptoms (as measured by a total withdrawal score) for various treatment and control protocols in a rat model of morphine withdrawal syndrome.

According to the present invention, ibudilast can be used to reduce this undesired glial activation. Ibudilast crosses the blood-brain barrier when administered systemically (Sugiyama et al. (1993) *No To Shinkei* 45(2): 139-42; see also FIG. 2 herein), eliminating the need for more invasive methods of administration in order to access central sites of inflammation involved in pathogenesis of morphine dependence and withdrawal. While certain agents like minocycline and fluorocitrate may have some activity preventing glial activation, they are unacceptable for human therapy. Fluorocitrate is unacceptable because it can block glial uptake of excitatory amino acids (Berg-Johnsen et al. (1993) *Exp. Brain Res.* 96(2):241-6), an essential function of glia in the maintenance of normal CNS homeostasis, and extended duration or increased doses of fluorocitrate cause seizures. Willoughby J. O., et al. (2003) *J. Neurosci. Res.* 74(1):160-66; Homfeldt, C. S. and Larson, A. A. (1990) *Eur. J Pharmacol.* 179(3):307-13. While minocycline may be useful in preventing glial activation, it does not appear to be able to reverse extant situations. Raghavendra et al. (2003) *J. Pharmacol. and Exp. Therapeutics* 306: 624-30; Ledeboer, A., et al. (2005) *Pain* 115:71-83.

Taken together, glia and their pro-inflammatory or neuromodulatory products may present opportunities for new strategies for control of morphine withdrawal. In one embodiment of the present invention, ibudilast is used to block the release of pro-inflammatory cytokines and neuromodulatory substances. Ibudilast is a potent suppressor of glial activation. Mizuno et al. (2004) *Neuropharmacology* 46:404-11. In a dose-dependent manner, ibudilast suppressed the production of nitric oxide (NO), reactive oxygen species, interleukin (IL)-1β, IL-6, and tumor necrosis factor (TNF) and enhanced the production of the inhibitory cytokine, IL-10, and additional neurotrophic factors, including nerve growth factor (NGF), glia-derived neurotrophic factor (GDNF), and neurotrophin (NT)-4 in activated microglia.

In one embodiment of the present invention, ibudilast is administered systemically or intrathecally in human subjects for the treatment of morphine withdrawal syndromes.

In other embodiments, ibudilast is administered by systemic (e.g. oral) or central (e.g. intrathecal) routes to attenuate neuropathological elements of morphine withdrawal.

Additional information is available in the following publications, the disclosures of which are hereby incorporated by reference in their entireties: Obernolte, R., et al. (1993) *Gene* 129:239-47; Rile, G., et al. (2001) *Thromb. Res.* 102:239-46; Souness, J. E., et al. (1994) *Br. J. Pharmacol.* 111:1081-88; Suzumura, A., et al. (1999) *Brain Res.* 837:203-12; Takuma, K., et al. (2001) *Br. J. Pharmacol.* 133:841-848.

Ibudilast may also be administered in combination with one or more other agents as part of a comprehensive opioid withdrawal treatment protocol. Such agents include, but are not limited to, the following agents:

Naltrexone (17-(cyclopropylmethyl)-4,5α-epoxy-3,14-dihydroxymorphinan-6-one, CAS No. 16676-29-2 (HCl)) has the molecular formula $C_{20}H_{23}NO_4$ and a molecular weight of 341.4.

Metoclopramide (4-amino-5-chloro-N-(2-diethylaminoethyl)-2-methoxy-benzamide, CAS No. 364-62-5) has the molecular formula $C_{14}H_{22}ClN_3O_2$ and a molecular weight of 299.8.

Loperamide (4-[4-(4-chlorophenyl)-4-hydroxy-1-piperidyl]-N,N-dimethyl-2,2-diphenyl-butanamide, CAS No. 53179-11-6) has the molecular formula $C_{29}H_{33}ClN_2O_2$ and a molecular weight of 477.04.

Diazepam (10-chloro-6-methyl-2-phenyl-3,6-diazabicyclo[5.4.0]undeca-2,8,10,12-tetraen-5-one, CAS No. 439-14-5) has the molecular formula $C_{16}H_{13}ClN_2O$ and a molecular weight of 284.74.

Clonidine (2-(2,6-dichlorophenylamino)-2-imidazoline hydrochloride, CAS No. 4205-90-7) has the molecular formula $C_9H_9Cl_2N_3HCl$ and a molecular weight of 266.56.

Paracetemol (N-(4-hydroxyphenyl)ethanamide, CAS No. 103-90-2), also referred to as acetaminophen, has the molecular formula $C_8H_9NO_2$ and a molecular weight of 151.2.

Pharmaceutical Compositions for Treating Addiction

Ibudilast

Ibudilast is a small molecule drug (molecular weight of 230.3) having the structure shown below.

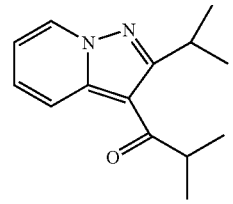

I

Ibudilast is also found under ChemBank ID 3227, CAS #50847-11-5, and Beilstein Handbook Reference No. 5-24-03-00396. Its molecular formula corresponds to [$C_{14}H_{18}N_2O$]. Ibudilast is also known by various chemical names which include 2-methyl-1-(2-(1-methylethyl)pyrazolo(1,5-a)pyridin-3-yl)1-propanone; 3-isobutyryl-2-isopropylpyrazolo(1,5-a)pyridine]; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and the brand name Ketas®. Ibudilast, as referred to herein, is meant to include any and all pharmaceutically acceptable salt forms thereof, prodrug forms (e.g., the corresponding ketal), and the like, as appropriate for use in its intended formulation for administration.

Ibudilast is a non-selective nucleotide phosphodiesterase (PDE) inhibitor (most active against PDE-3, PDE-4, PDE-10, and PDE-11 (Gibson et al. (2006) Eur. J. Pharmacology 538: 39-42)), and has also been reported to have LTD4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are 11 families of PDEs: $Ca^{2+}$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); specific PDE (PDE8); high affinity cGMP-specific PDEs (PDE9); and mixed cAMP and cGMP PDEs (PDE10, PDE11).

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), different physical forms (e.g., crystalline solids, amorphous solids), metabolites, and the like.

Formulation Components

Excipients/Carriers

Optionally, in addition to ibudilast, the compositions of the invention may further comprise one or more pharmaceutically acceptable excipients or carriers. Exemplary excipients include, without limitation, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the invention may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the invention are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

An ibudilast-containing composition of the invention may also include an antimicrobial agent, e.g., for preventing or deterring microbial growth. Non-limiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

A composition of the invention may also contain one or more antioxidants. Antioxidants are used to prevent oxidation, thereby preventing the deterioration of the drug(s) or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the invention may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient. In general, the amount of excipient present in an ibudilast composition of the invention is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

Other Actives

A formulation (or kit) in accordance with the invention may contain, in addition to ibudilast, one or more additional active agents effective in treating addiction. Preferably, the active agent is one that possesses a mechanism of action different from that of ibudilast. Such actives include naltrexone, metoclopramide, loperamide, diazepam, clonidine, lofexidine, and paracetemol.

Sustained Delivery Formulations

Preferably, the compositions are formulated in order to improve stability and extend the half-life of ibudilast. For example, ibudilast may be delivered in sustained-release formulations. Controlled or sustained-release formulations are prepared by incorporating ibudilast into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast can be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., *Pharm. Res.* (1993) 10:362-368; and McGee et al., *J. Microencap.* (1996).

Delivery Forms

The ibudilast compositions described herein encompass all types of formulations, and in particular, those that are suited for systemic or intrathecal administration. Oral dosage forms include tablets, lozenges, capsules, syrups, oral suspensions, emulsions, granules, and pellets. Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored, and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx™ (Aradigm), the Ultravent® (Mallinkrodt), and the Acorn II® (Marquest Medical Products). A composition of the invention may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the invention are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the invention may also be a sustained release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the invention may optionally include other agents conventional in the pharmaceutical arts and particular type of formulation being employed, for example, for oral administration forms, the composition for oral adminsitration may also include additional agents as sweeteners, thickeners or flavoring agents.

The compositions of the present invention may also be prepared in a form suitable for veterinary applications.

Method of Administration

As set forth above, preferred methods of delivery of ibudilast-based therapeutic formulations for the treatment of addictions include systemic and localized delivery, i.e., directly into the central nervous system. Such routes of administration include but are not limited to, oral, intra-arterial, intrathecal, intramuscular, intraperitoneal, subcutaneous, intravenous, intranasal, and inhalation routes.

More particularly, an ibudilast-containing formulation of the present invention may be administered for therapy by any suitable route, including without limitation, oral, rectal, nasal, topical (including transdermal, aerosol, buccal and sublingual), vaginal, parenteral (including subcutaneous, intramuscular, intravenous and intradermal), intrathecal, and pulmonary. The preferred route will, of course, vary with the condition and age of the recipient, the particular neuralgia-associated syndrome being treated, and the specific combination of drugs employed.

One preferred mode of administration for delivery of ibudilast is directly to neural tissue such as peripheral nerves, the retina, dorsal root ganglia, neuromuscular junction, as well as the CNS, e.g., to target spinal cord glial cells by injection into, e.g., the ventricular region, as well as to the striatum (e.g., the caudate nucleus or putamen of the striatum), spinal cord and neuromuscular junction, with a needle, catheter or related device, using neurosurgical techniques known in the art, such as by stereotactic injection (see, e.g., Stein et al., *J. Virol.* 73:3424-3429, 1999; Davidson et al., *PNAS* 97:3428-3432, 2000; Davidson et al., *Nat. Genet.* 3:219-223, 1993; and Alisky and Davidson, *Hum. Gene Ther.* 11:2315-2329, 2000).

A particularly preferred method for targeting spinal cord glia is by intrathecal delivery, rather than into the cord tissue itself.

Another preferred method for administering the ibudilast-based compositions of the invention is by delivery to dorsal root ganglia (DRG) neurons, e.g., by injection into the epidural space with subsequent diffusion to DRG. For example, an ibudilast-based composition can be delivered via intrathecal cannulation under conditions where ibudilast is diffused to DRG. See, e.g., Chiang et al., *Acta Anaesthesiol. Sin.* (2000) 38:31-36; Jain, K. K., *Expert Opin. Investig. Drugs* (2000) 9:2403-2410.

Yet another mode of administration to the CNS uses a convection-enhanced delivery (CED) system. In this way, ibudilast can be delivered to many cells over large areas of the CNS. Any convection-enhanced delivery device may be appropriate for delivery of ibudilast. In a preferred embodiment, the device is an osmotic pump or an infusion pump. Both osmotic and infusion pumps are commercially available from a variety of suppliers, for example Alzet Corporation, Hamilton Corporation, Alza, Inc., Palo Alto, Calif.). Typically, an ibudilast-based composition of the invention is delivered via CED devices as follows. A catheter, cannula or other injection device is inserted into CNS tissue in the chosen subject. Stereotactic maps and positioning devices are available, for example from ASI Instruments, Warren, Mich. Positioning may also be conducted by using anatomical maps obtained by CT and/or MRI imaging to help guide the injection device to the chosen target. For a detailed description regarding CED delivery, see U.S. Pat. No. 6,309,634, incorporated herein by reference in its entirety.

An ibudilast composition of the invention, when comprising more than one active agent, may be administered as a single combination composition comprising a combination of ibudilast and at least one additional active agent effective in the treatment of addiction. In terms of patient compliance and ease of administration, such an approach is preferred, since patients are often adverse to taking multiple pills or dosage forms, often multiple times daily, over the duration of treatment. Alternatively, albeit less preferably, the combination of the invention is administered as separate dosage forms. In instances in which the drugs comprising the therapeutic composition of the invention are administered as separate dosage forms and co-administration is required, ibudilast and each of the additional active agents may be administered simultaneously, sequentially in any order, or separately.

Kits

Also provided herein is a kit containing at least one combination composition of the invention, accompanied by instructions for use.

For example, in instances in which each of the drugs themselves are administered as individual or separate dosage forms, the kit comprises ibudilast in addition to each of the drugs making up the composition of the invention, along with instructions for use. The drug components may be packaged in any manner suitable for administration, so long as the packaging, when considered along with the instructions for administration, clearly indicates the manner in which each of the drug components is to be administered.

For example, for an illustrative kit comprising ibudilast and naltrexone, the kit may be organized by any appropriate time period, such as by day. As an example, for Day 1, a representative kit may comprise unit dosages of each of ibudilast and naltrexone. If each of the drugs is to be administered twice daily, then the kit may contain, corresponding to Day 1, two rows of unit dosage forms of each of ibudilast and naltrexone, along with instructions for the timing of administration. Alternatively, if one or more of the drugs differs in the timing or quantity of unit dosage form to be administered in comparison to the other drug members of the combination, then such would be reflected in the packaging and instructions. Various embodiments according to the above may be readily envisioned, and would of course depend upon the particular combination of drugs, in addition to ibudilast, employed for treatment, their corresponding dosage forms, recommended dosages, intended patient population, and the like. The packaging may be in any form commonly employed for the packaging of pharmaceuticals, and may utilize any of a number of features such as different colors, wrapping, tamper-resistant packaging, blister paks, dessicants, and the like.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated, the judgment of the health care professional, and particular combination being administered.

Therapeutically effective amounts can be determined by those skilled in the art, and will be adjusted to the requirements of each particular case. Generally, a therapeutically effective amount of ibudilast will range from a total daily dosage, for example in humans, of about 0.1 and 500 mg/day, more preferably, in an amount between 1 and 200 mg/day, 1 and 100 mg/day, 1 and 40 mg/day, or 1 and 20 mg/day. Administration can be one to three times daily for a time course of one day to several days, weeks, months, and even years, and may even be for the life of the patient.

Practically speaking, a unit dose of any given composition of the invention or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

III. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Pharmacokinetics and Tissue Distribution of Ibudilast in Rat

Ibudilast pharmacokinetics and distribution into plasma, muscle, brain, and spinal cord were assessed as follows.

Experimental Procedures

Ibudilast for administration to rats was prepared in 15% ethanol/saline. Drug stability and concentration were validated by HPLC/MS/MS.

Pathogen-free adult male Sprague-Dawley rats (280-350 g; Harlan Labs) were used in all experiments. Rats were housed in temperature (23+/−3° C.) and light (12:12 light: dark; lights on at 0700 hr) controlled rooms with standard rodent chow and water available ad libitum. Behavioral testing was performed during the light cycle.

Rats (n=3/group) were administered 5 mg/kg ibudilast, i.p., and plasma, muscle, brain, and spinal cord were harvested at 5, 15, 60, 180, and 420 minutes post administration. The concentration of ibudilast in tissue samples was determined as follows. A solution of ibudilast (Haorui) at 0.5 mg/ml in DMSO was used as the working reference stock solution. Calibration standards in plasma were prepared by diluting each 0.5 mg/ml stock 1 in 100 into rat plasma to 5000 ng/ml (5 µl+495 µl), and then diluted further to 2.29 ng/ml by 3-fold serial dilution with plasma. Standards were used as low, mid and high QC samples, respectively.

Calibration standards, QC and plasma study samples were prepared for HPLC injection by precipitating 25 µl of plasma with three volumes (75 µl) of ice cold acetonitrile containing 50 ng/ml diphenhydramine and 100 ng/ml dextromethorphan as the internal standards. Tissue study samples were prepared for HPLC injection by adding 1 µl of water per mg of tissue plus three volumes (relative to water) of ice cold acetonitrile containing 50 ng/ml diphenhydramine and 100 ng/ml dextromethorphan as the internal standards, then homogenizing with an electric homogenizer. Following centrifugation at 6100 g for 30 minutes, 40 µl of each supernatant was diluted with 200 µl of 0.2% formic acid in water and analyzed under the following LC/MS/MS conditions:

HPLC: Shimadzu VP System
Mobile Phase: 0.2% formic acid in water (A) and in methanol (B)
Column: 2×10 mm Peeke Scientific DuraGel G $C_{18}$ guard cartridge
Injection Volume: 100 µl
Gradient: 5-95% B in 2 minutes after a 0.75 minute wash
Flow Rate: 400 µl/min
Mass Spectrometer: Applied Biosystems/MDS SCIEX API 3000
Interface: TurboIonSpray (ESI) at 400° C.
Ionization Mode: Positive Ion
Q1/Q3 Ions: 231.2/161.2 for Ibudilast (IBUDILAST)

Results

As shown in FIG. 1, intraperitoneal administration of ibudilast yielded good plasma concentrations that declined from Cmax in a biphasic manner. Ibudilast was well distributed to peripheral (e.g. muscle) and central (e.g. brain and spinal cord) tissues. The maximal concentration (Cmax) in plasma and CNS tissues was ~1 µg/mL following i.p. administration of ~5 mg/kg ibudilast formulated as described. The elimination half-life ranged from 100-139 min in all tissue compartments.

EXAMPLE 2

Eefficacy of Ibudilast in a Rat Model of Morphine Withdrawal

A study lasting approximately one week was performed to assess the potential for ibudilast co-treatment to reduce the intensity and duration of morphine withdrawal behaviors.

Experimental procedures

Ibudilast was obtained as a pure powder from Sigma (St. Louis, Mo.) or Haorui Pharma (Edison, N.J.) and prepared daily as a solution for intraperitoneal (i.p.) administration. Previous range-finding tolerability and efficacy studies in other neurological models indicated that ibudilast was well-tolerated intraperitoneally at dose levels up to 15 mg/kg twice a day (bid) for multiple days. Ibudilast efficacy following intraperitoneal administration was representative of other systemic routes of administration such as oral treatment. An appropriate amount of ibudilast was dissolved in 100% polyethylene (PEG) 400 (Sigma) and then diluted down to a final concentration of 35% PEG400 in sterile saline (0.9% for injection).

Ibudilast was administered at 2.5 mg/kg (0.9 ml/kg of 2.8 mg/ml in 35% PEG/saline), or 7.5 mg/kg (2.7 ml/kg of 2.8 mg/ml in 35% PEG/saline) each morning (typically 9 am) and afternoon (typically 4 pm). Drug stability and concentration were validated by HPLC/MS/MS.

Pathogen-free adult male Sprague-Dawley rats (280-350 g; Harlan Labs) were used in all experiments. Rats were housed in temperature (23+/×3° C.) and light (12:12 light: dark; lights on at 0700 hr) controlled rooms with standard rodent chow and water available ad libitum. Behavioral testing was performed during the light cycle. Approval of the Institutional Animal Care and Use Committee at University of Colorado was obtained for all procedures.

The schedule for morphine treatment (via subcutaneous injections) was as follows: Day 1: 5 mg/kg at 1000 hr, 5 mg/kg at 1300 hr, 5 mg/kg at 1700 hr; Day 2: 5 mg/kg at 1000 hr, 12.5 mg/kg at 1700 hr; Day 3: 15 mg/kg at 1000 hr; Day 4: 17.5 mg/kg at 1000 hr; Day 5: 5 mg/kg at 1000 hr, 17.5 mg/kg at 1200 hr.

Rats received morphine according to the schedule above, plus either saline (n=4), PEG vehicle (n=5), 2.5 mg/kg ("low dose") ibudilast (n=4), or 7.5 mg/kg ("high dose") ibudilast (n=5) according to the following schedule: The two days prior to start of morphine: daily at 1000 hr and 1700 hr; Days 1-4 of morphine regimen: daily at 1000 hr and 1700 hr; Day 5 of morphine regimen: at 1000 hr and 1200 hr. Rats then received 5 mg/kg naloxone at 1245 hr on Day 5, 45 minutes after their last dose of morphine and/or ibudilast, saline or vehicle.

The withdrawal signs measured were: (1) abnormal posturing (an animal presses his abdomen and lower jaw against the floor of the cage); (2) exploration (an animal circles around the cage, thrusting its head in several directions and examining its surroundings); (3) jumping; (4) cleaning (grooming); (5) rearing (an animal stands on its hindpaws with the forepaws off the ground). The total incidence of all five of the stereotyped behaviors in 10 minutes of observation was scored according to the following scale: 0=none displayed; 1=1-5 episodes of a behavior; 2=6-10 episodes of a behavior; 3=11-15 episodes of a behavior; 4=16-20 episodes of a behavior 5=21 or more episodes of a behavior.

Withdrawal scores were measured by blinded observers in 10 minute blocks for 60 minutes immediately after naloxone precipitated withdrawal was initiated. The observations were pooled from 1-10 minutes, 11-20 minutes, 21-30 minutes, 31-40 minutes, 41-50 minutes, 51-60 minutes for each individual rat after naloxone administration, giving six time points. The average score (for each time point) for all animals within an experimental group was reported as the "total withdrawal score" in FIGS. 2A-2D.
Results FIGS. 2A-2D demonstrate that ibudilast treatment was effective at reducing both the magnitude and duration of classic physiological manifestations of naloxone-precipitated morphine withdrawal syndrome. While the PEG vehicle had no effect on these behaviors, compared to saline controls (FIG. 2A), ibudilast revealed a dose dependent reduction of these behaviors (FIGS. 2B-2D). Although the low dose of ibudilast (2.5 mg/kg) had no effect compared to saline controls (FIG. 2C), the high dose of ibudilast (7.5 mg/kg) remarkably attenuated behavioral signs of withdrawal (FIG. 2B; presented as a bar graph in FIG. 2D).

EXAMPLE 3

Ibudilast Suppression of Dopamine Release in the Nucleus Accumbens

Experimental Procedures

Dopamine release in the nucleus accumbens is thought to mediate the "reward" associated with drugs of abuse. Ibudilast suppressed dopamine release in the nucleus accumbens, as measured by in vivo microdialysis. Systemic ibudilast (7.5 mg/kg b.i.d.) was co-administered with systemic morphine to rats (6 rats/group) across 5 days, using the morphine regimen described in Example 1. On the morning of the 6$^{th}$ day, rats received ibudilast one hour prior to initiation of baseline sampling. After 3 baseline samples (20 minute inter-sample interval), morphine was administered to all rats. Dialysis samples were collected at 20 minute intervals for 180 minutes. To test behavioral withdrawal and reversal of morphine-induced dopamine, all rats were administered the opioid antagonist naloxone after the 60 minute sample time was completed.

Results

Figure 3:
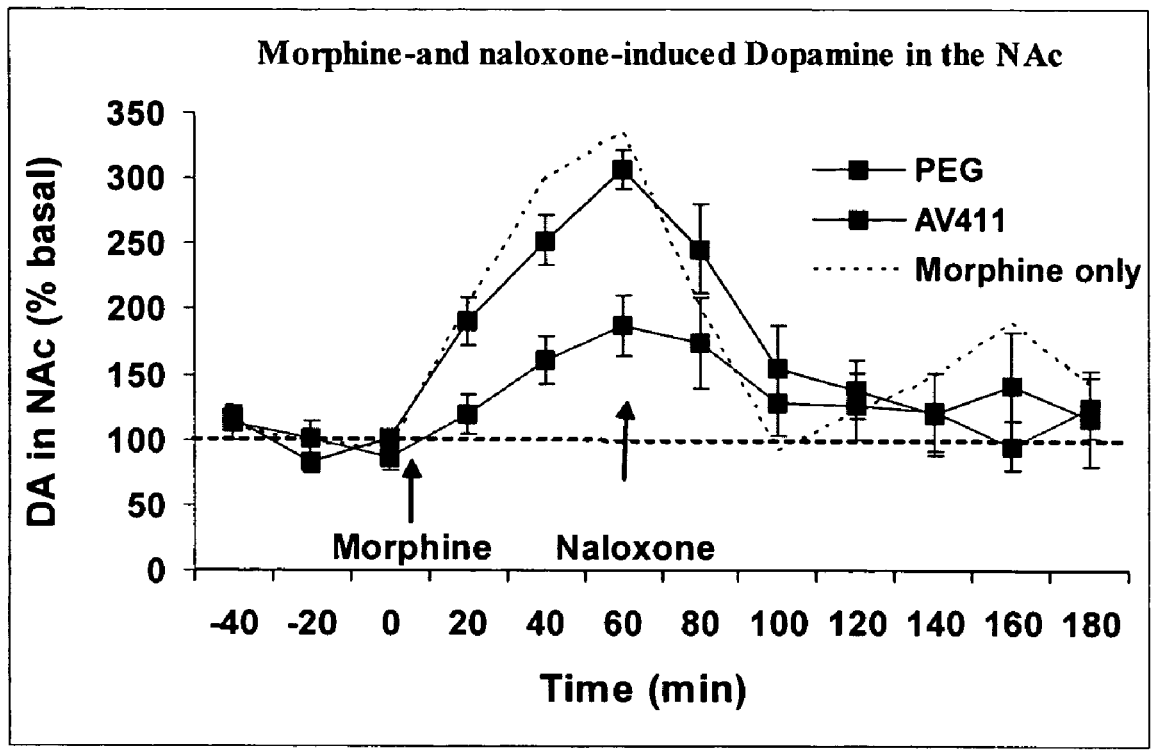
FIG. 3 shows the levels of dopamine (DA) in the nucleus accumbens (NAc) of rats treated with morphine in the presence and absence of ibudilast (AV411).
Figure 4:
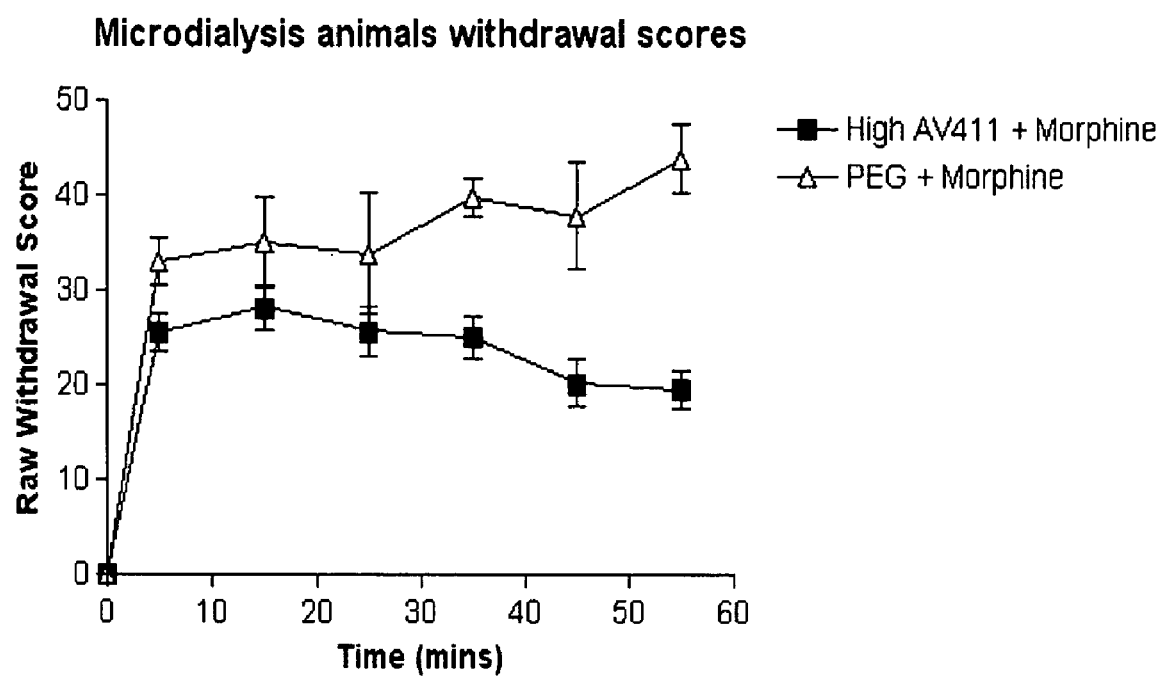
FIG. 4 compares the withdrawal behavior during microdialysis of rats which were treated with morphine in the presence and absence of ibudilast (AV411).

As shown in FIG. 3, rats treated with ibudilast exhibited significantly suppressed indicators or mediators of "reward" as evidenced by suppressed release of dopamine into the nucleus accumbens in response to morphine. Ibudilast did not decrease basal levels of dopamine. The opioid antagonist naloxone reversed the morphine-induced dopamine release, which shows that the dopamine release was indeed due to the effects of morphine. Rats repetitively co-administered ibudilast and morphine showed suppressed naloxone-induced behavioral withdrawal signs, compared to rats repetitively administered PEG-saline vehicle and morphine (see FIG. 4).

Conclusion

The results of both brain microdialysis dopamine levels and concomitant opiate withdrawal behavioral responses indicate that ibudilast treatment of rats significantly reduces a neurochemical mediator (dopamine) of reward or salience and behavioral manifestations of opiate dependence. Such results imply that ibudilast will be useful for the treatment of multiple forms of dependence.

EXAMPLE 4

Ibudilast Reduces the Development of Morphine Dependence and Central Glial Cell Activation Experimental Procedures Rats (n=10/group) received morphine according to the schedule described above in Example 2, plus either saline, PEG vehicle, 2.5 mg/kg ("low dose") ibudilast, or 7.5 mg/kg ("high dose") ibudilast according to the following schedule: The two days prior to start of morphine: daily at 1000 hr and 1700 hr; Days 1-4 of morphine regimen: daily at 1000 hr and 1700 hr; Day 5 of morphine regimen: at 1000 hr and 1200 hr. Rats then received 5 mg/kg naloxone at 1245 hr on Day 5, 45 minutes after their last dose of morphine and/or ibudilast, saline or vehicle.

Following scoring of withdrawal behaviors animals received an intraperitoneal injection of 0.8 ml of 50 mg/ml sodium pentobarbital, and once anesthetized, animals were transcardially perfused. Half of each treatment group were perfused with saline and half with 4% paraformaldehyde. Spinal cord and brains were collected (saline perfusion for protein and mRNA quantification and paraformaldehyde perfusion for immunohistochemistry). Samples collected from saline perfused animals were flash frozen in liquid nitrogen and stored at −80° C. Paraformaldehyde perfused samples were stored in 4% paraformaldehyde for 48 hours and then transferred to 30% sucrose (0.1% azide) until tissue sectioning.

Immunoreactivity for OX-42 (antibody that recognizes complement type 3 receptors, e.g., CD11b) and/or glial fibrillary acidic protein (GFAP), microglial and astrocyte activation markers, respectively, were assessed. Sections (20 µm) were treated with 0.3% $H_2O_2$ in Tris-buffered saline (TBS) for 20 minutes at room temperature to suppress endogenous peroxidase activity. Sections were then incubated overnight at 4° C. in monoclonal mouse anti-rat OX-42 (1:100; Pharmingen, San Diego, Calif.) or monoclonal mouse anti-rat GFAP antibody (1:200; Chemicon, Temecula, Calif.) in TBS with 2% normal goat serum and 0.5% Triton-X-100. Subsequently, sections were incubated with the appropriate secondary biotinylated antibodies (1:400; Jackson ImmunoResearch, West Grove, Pa.) for 2 hours at room temperature, incubated in avidin-biotin complex solution (ABC; 1:200; Vector Laboratories, Burlingame, Calif.) for 2 hours at room temperature, followed by reaction with 0.5 mg/ml 3,3'-diaminobenzidine tetrahydrochloride (DAB; Sigma). Finally, sections were dried, dehydrated, and coverslipped with Permount. Staining was evaluated by light microscopy. Densitometry of immunohistochemical staining was subsequently evaluated using computer software (NIH image).

Amplification of cDNA was performed using the QUANTITECT SYBR GREEN PCR kit (Qiagen, Valencia, Calif.) in ICYCLER IQ 96-well PCR plates (Bio-Rad, Hercules, Calif.) on a MYIQ single color real-time PCR detection system (Bio-Rad). The reaction mixture (26 µl) was composed of 1× QUANTITECT SYBR GREEN PCR master mix (containing the fluorescent dye SYBR green I, 2.5 mM $MgCl_2$, dNTP mix, and HOTSTART Taq DNA polymerase), 10 nM fluorescein, 500 nM each of forward and reverse primers, 25 ng cDNA and nuclease-free $H_2O$. Reactions were done in triplicate (n=3-6 animals/group). The reaction conditions were an initial 15 minutes at 95° C., followed by 40 cycles of 15 seconds at 94° C., 30 seconds at 55-60° C., and 30 seconds at 72° C. Melt curve analyses were conducted to assess uniformity of product formation, primer-dimer formation, and amplification of non-specific products. Linearity and efficiency of PCR amplification were assessed using standard curves generated by increasing amounts of cDNA. SYBR green l fluorescence (PCR product formation) was monitored in real time using the MYIQ single color real-time PCR detection system (Bio-Rad). Threshold for detection of PCR product was set in the log-linear phase of amplifon of non-specific products. Linearity and efficiency of PCR amplification were assessed using standard curves generated by increasing amounts of cDNA. SYBR green 1 fluorescence (PCR product formation) was monitored in real time using the MYIQ single color real-time PCR detection system (Bio-Rad). Threshold for detection of PCR product was set in the log-linear phase of amplification and the threshold cycle (CT, the number of cycles to reach threshold of detection) was determined for each reaction. The levels of the target mRNAs were quantified relatively to the level of the housekeeping gene glyceraldehyde-3-phosphate-dehydrogenase (GAPDH) using the comparative CT ($\Delta$CT) method (Livak and Schmittgen, 2001). Expression of the housekeeping gene was not significantly altered by experimental treatment.

Results

A. Weight Changes

Animals treated with ibudilast showed reduced body weight loss compared to animals treated with vehicle during the first 2 days of treatment (9.3±6.3 g for animals treated with 7.5 mg/kg ibudilast; 10.4±5.6 g for animals treated with 2.5 mg/kg ibudilast; and 1±4.4 g for animals treated with vehicle). Therefore, data were normalized for weights on the morning animals started morphine treatment (thereby removing the ibudilast induced weight loss during the first 2 days). On day 7, the morphine induced weight loss was 13.3±7.1g in animals treated with 7.5 mg/kg ibudilast, 16.6±5.7g in animals treated with 2.5 mg/kg ibudilast, and 18.2±6.6g in animals treated with vehicle. Body weight loss is a classic and objective marker of withdrawal in rat opiate models and attenuation by high dose ibudilast is supportive of physiological benefit during opiate withdrawal.

B. Withdrawal Behaviors

Figure 5:
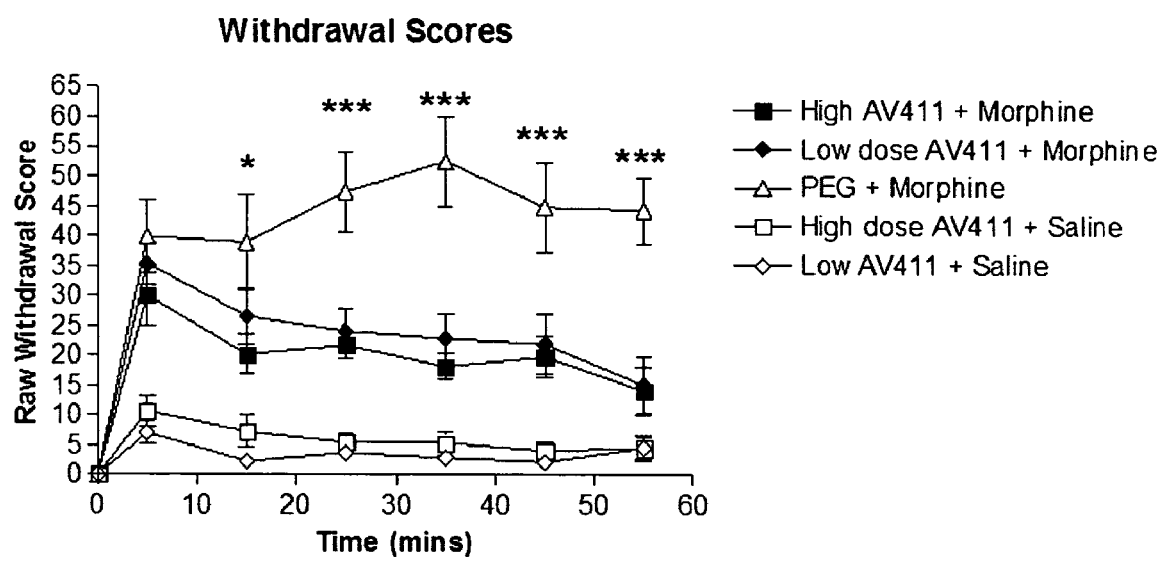
FIG. 5 compares naloxone-induced withdrawal behavior of rats treated with morphine and ibudilast at a low dosage (2.5 mg/kg), ibudilast at a high dosage (7.5 mg/kg), or vehicle (PEG).

As shown in FIG. 5, treatment with ibudilast at dosages of 2.5 mg/kg and 7.5 mg/kg resulted in a dramatic reduction of naloxone precipitated withdrawal behaviors during a 60 minute observation period. On an individual behavior basis, treatment with ibudilast resulted in reductions in all behaviors except for rearing, exploration and wet dog shakes, whereas no change was observed in animals treated with vehicle. Data are presented in FIG. 5 as the sum of the total withdrawal behaviors observed during each ten minute block for all animals in the study (n=10/treatment group).

C. Brain Immunohistochemistry

Figure 6:
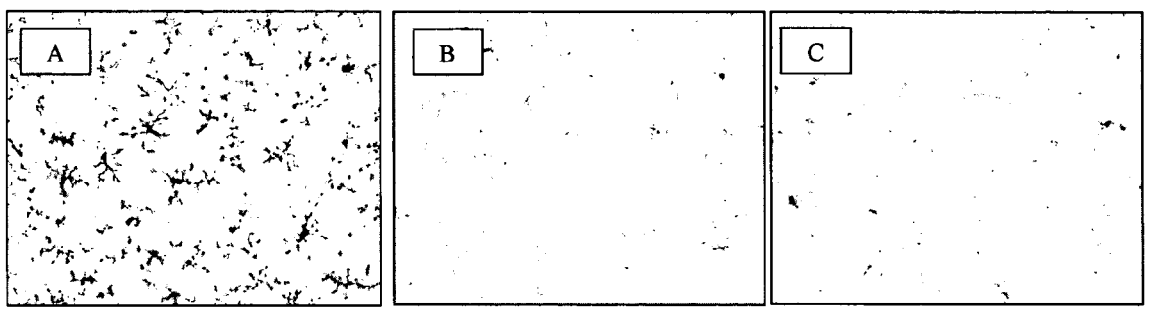
FIGS. 6A-6C show immunohistochemical analyses of brain samples collected from rats.
Figure 7:
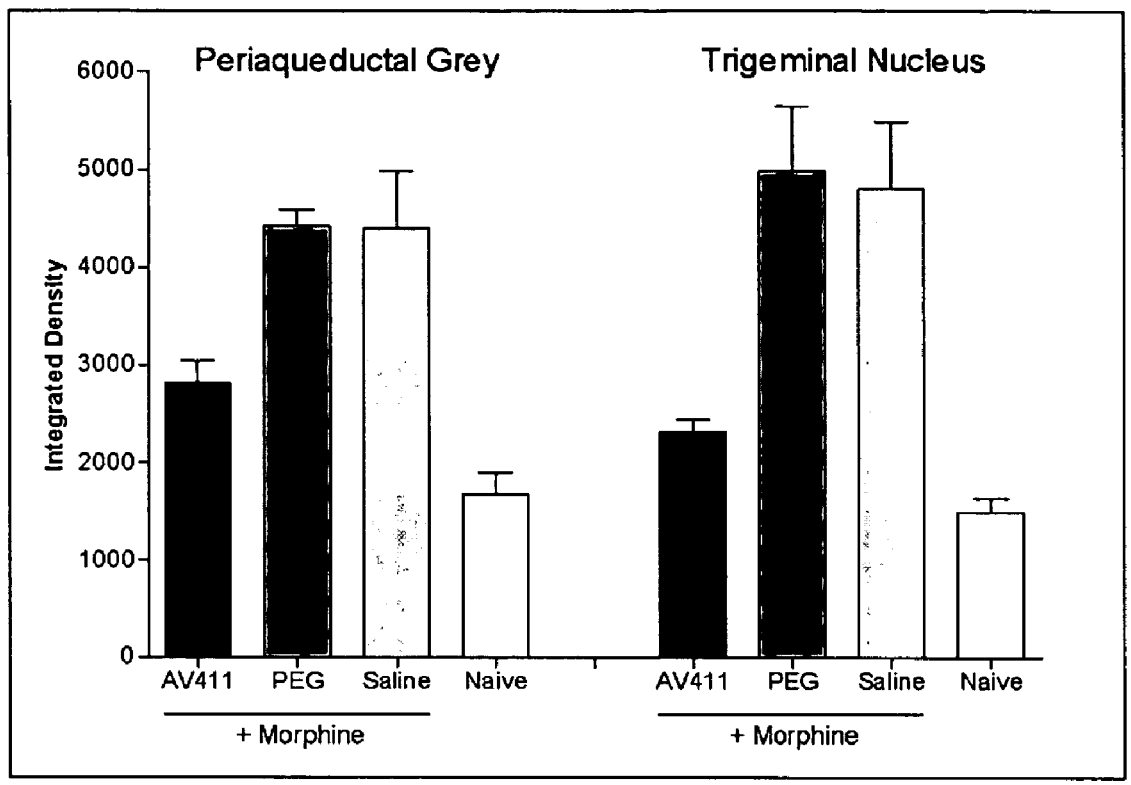
FIG. 7 shows a densitometry analysis of the microglial activation marker CD11b from brain samples. Ibudilast caused a significant reduction in the microglial activation marker CD11b in 2 brain regions, the periaqueductal grey and the brain homologue of the spinal dorsal horn, the trigeminal nucleus.

Immunohistochemical analysis was conducted on brain samples collected from rats following paraformaldehyde perfusion. Microglial activation marker CD11b and astrocyte marker GFAP were investigated. As can be seen in FIG. 6, chronic morphine administration caused visible upregulation of the microglia activation marker CD11b. Treatment with ibudilast dramatically reduced the increase in the CD11b marker. Densitometry analysis (FIG. 7) revealed that ibudilast caused a significant reduction in the microglial activation marker CD11b in 2 brain regions, the periaqueductal grey and the brain homologue of the spinal dorsal horn, the trigeminal nucleus.

D. mRNA Analysis of Brain Nuclei

Figure 8:
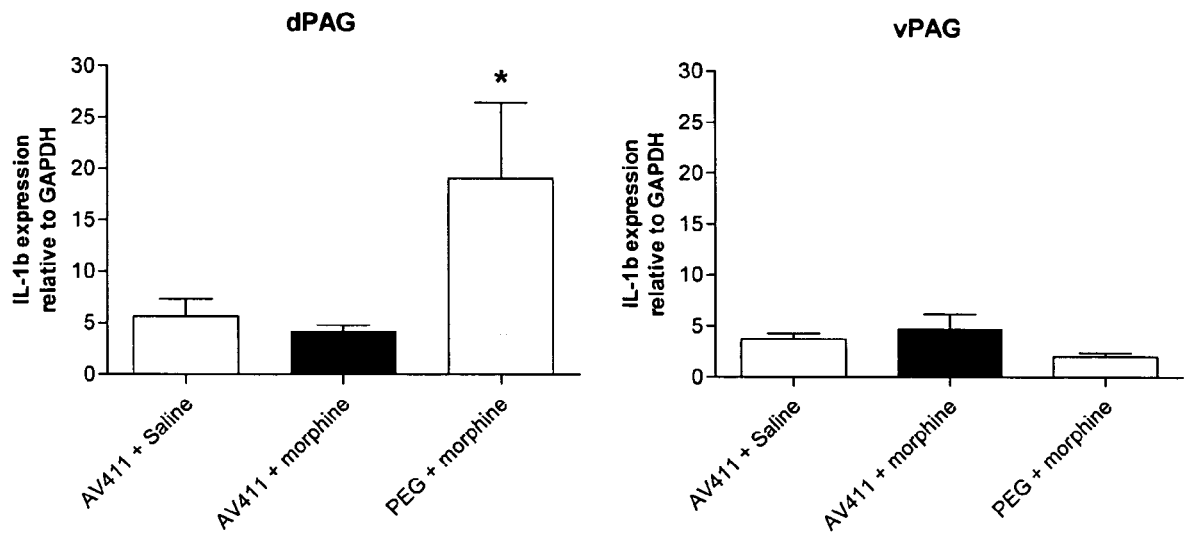
FIG. 8 shows a comparison of IL-1 expression in brain tissue collected from animals treated with ibudilast, ibudilast and morphine, and morphine and vehicle (PEG). Morphine increased IL-1 mRNA in the dorsal but not the ventral periaqueductal grey region of the brain. Ibudilast blocked the morphine induced increase in IL-1 mRNA in the dorsal periaqueductal grey region.

Interleukin-1 mRNA from the brain tissue samples was quantitated. Morphine caused a dramatic increase in interleukin-1 mRNA in the dorsal, but not the ventral periaqueductal grey region (FIG. 8). Ibudilast completely blocked the morphine induced increase in interleukin-1 mRNA in the dorsal periaqueductal grey region.

Conclusion

Ibudilast administration during morphine treatment results in significantly reduced glial cell activation and proinflammatory cytokine production in the brain of treated animals. Upon naxolone-precipitated withdrawal, animals receiving ibudilast display significantly reduced behavioral responses indicating that ibudilast treatment attenuates the neuroinflammation and behavioral symptoms associated with the syndrome of opiate withdrawal.

EXAMPLE 5

Ibudilast Reverses Morphine Dependence and Spontaneous Opioid Withdrawal

Experimental Procedures

Pathogen-free adult male Sprague-Dawley rats were used in all experiments. Rats (350-375 g at the time of arrival; Harlan Labs, Madison, Wis.) were housed in temperature (23±3° C.) and light (12:12 light:dark; lights on at 0700 hours) controlled rooms with standard rodent chow and water available ad libitum. All procedures were approved by the Institutional Animal Care and Use Committee at the University of Colorado at Boulder. Upon arrival male Sprague Dawley rats (300-400g) were housed individually and allowed to acclimatize to the animal colony telemetry room for one week. 5×90 minute sessions of handling by investigators were performed during the following week.

Rats were anesthetized with isoflurane, and emitters for measuring core body temperature (MiniMitter, Sun River, Oreg.) were implanted in the peritoneal cavity. Gross motor movement was assessed by telemetry using the same emitters used for recording core body temperature. The emitter had to move for activity to be counted; thus, stationary movements such as grooming were not counted. Activity counts and core body temperature were measured every minute and movement averaged over 120 minutes was calculated (thereby smoothing the data). Recording of telemetry data occurred throughout the entire experiment. Periods of time when experimenters entered the housing room were eliminated from analyses as these produced increased activity and therefore error. At the time of telemetry implant, animals were implanted with 2 subcutaneous 2ML2 lumbar osmotic minipumps (Alzet, Cupertino, Calif.), which each pumped at about 5 il per hour for 14 days (hence a combined total of 10 µl per hour). One pump had a lead length of PE60 tubing pre-loaded with saline to delay the morphine delivery for 2 days. Therefore, the pumps delivered 6.25 mg of morphine (or saline) per day on days 1 and 2, then 12.5 mg per day from then onward. On day 12, animals began a 7 day twice daily ibudilast regimen (7.5 mg/kg or 2.5 mg/kg in 35% PEG in saline dose volume 2.5 ml/kg) or vehicle (35% PEG in saline) (completing with the final dose on the afternoon of day 18). The morning injection occurred between 8:45 AM and 9:15 AM, with the afternoon injection occurring between 4:45 PM and 5:15 PM. On day 14, the pumps were removed to precipitate spontaneous opioid withdrawal (in animals receiving morphine). Body weights were recorded prior to each dosing session to allow for accurate dose calculations and to track the opioid induced weight loss (also occurred on days when no dosing was conducted).

Results

Figure 9:
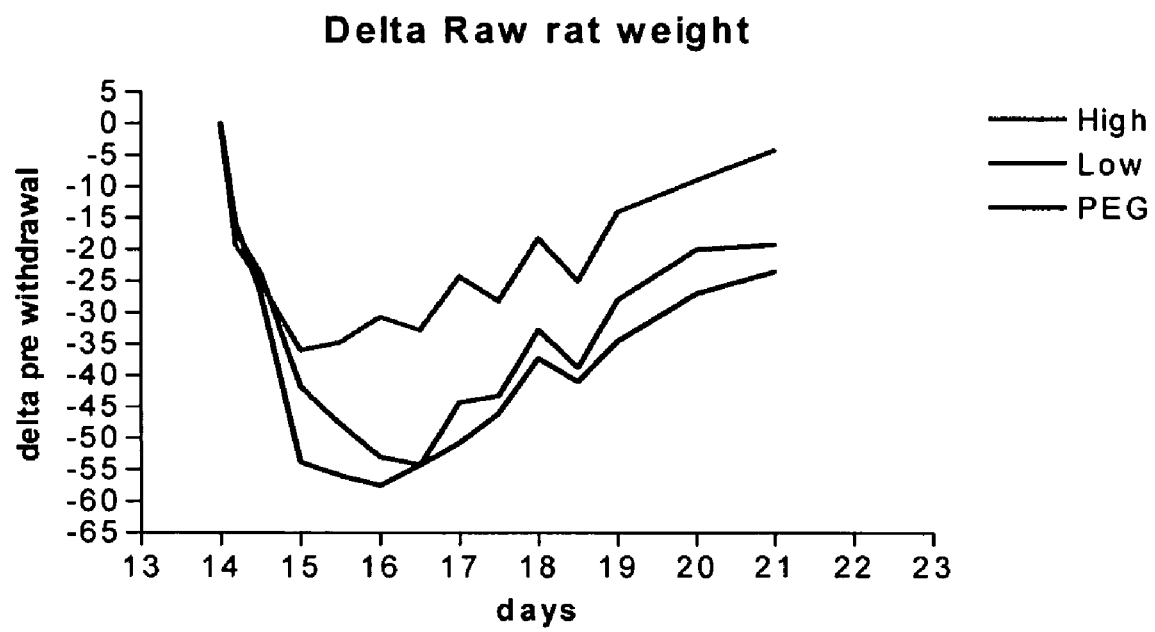
FIG. 9 shows ibudilast-attenuated weight loss in animals experiencing spontaneous opioid withdrawal.

Ibudilast protected animals from spontaneous opioid withdrawal induced weight loss. As shown in FIG. 9, only a trend towards improved weight change was observed at the lower dose of ibudilast, but at the higher dose, ibudilast substantially attenuated weight loss. The endpoint of weight loss attenuation is considered an important objective measurement of reduced withdrawal in rats.

EXAMPLE 6

Nucleus Accumbens Dopamine Microdialysis Following 5 Days of Treatment with Morphine and Ibudilast Experimental Procedures Pathogen-free adult male Sprague-Dawley rats were used in all experiments. Rats (300-325 g at the time of arrival; Harlan Labs, Madison, Wis.) were housed in temperature ($23\pm3°$ C.) and light (12:12 light:dark; lights on at 0700 hours) controlled rooms with standard rodent chow and water available ad libitum. All procedures were approved by the Institutional Animal Care and Use Committee at the University of Colorado at Boulder. Upon arrival male Sprague Dawley rats (300-400 g) were housed in pairs and allowed to acclimatize to the animal colony for one week. 5×90 minute sessions of handling by investigators and animal acclimatization to the microdialysis environment were performed during the following week.

Microdialysis guide cannula implantation was performed under halothane anaesthesia. CMA 12 guide cannulae (CMA Microdialysis) were aimed at either the right or left nucleus accumbens (AP=+1.7, LM=±0.8, DV=−6.0) in a counterbalanced fashion. Coordinates were from bregma using the atlas of Paxinos and Watson (1998). The guide cannulae and a tether screw (CMA Microdialysis) were anchored to the skull with three jeweler's screws and dental cement. Rats were individually housed after surgery and allowed to recover for one week.

Animals then began a 7 day dosing regimen (groups of 6 animals at a time, n=10 per treatment group). Throughout the 7 days animals received twice daily intraperitoneal injections of ibudilast (7.5 mg/kg or 2.5 mg/kg in 35% PEG in saline dose volume 2.5 ml/kg) or vehicle (35% PEG in saline). The morning injection occurred between 8:45 AM and 9:15 AM, with the afternoon injection occurring between 4:45 PM and 5:15 PM. On day 3 animals began a 5 day dependence regimen of morphine or vehicle (saline) (subcutaneous injections 1 ml/kg). When morphine was administered in the morning or afternoon, it occurred 30 minutes following the ibudilast injection. The dependence regimen consisted of Day 3: AM dose 5 mg/kg, noon dose 5 mg/kg, PM dose 5 mg/kg; Day 4: AM dose 7.5 mg/kg, PM dose 12.5 mg/kg; Day 5 AM dose 15 mg/kg; Day 6 AM dose 17.5 mg/kg; and Day 7 AM dose 22.5 mg/kg. Body weights were recorded prior to each dosing session to allow for accurate dose calculations and to track the opioid induced weight loss.

On the afternoon before microdialysis (day 6 following morphine and ibudilast administration) rats were transferred to the dialysis room that was on the same light-dark cycle as the colony room. Microdialysis probes (CMA 12, MW cut-off 20,000 Da, 2 mm active membrane) were inserted into the guide cannulae and rats were placed in separate Plexiglas infusion bowls with food and water available ad libitum. Ringers solution (147 mM NaCl, 2.97 mM CaCl, 4.02 mM KCl; Baxter) was perfused through the probes using a CMA infusion pump at a flow rate of 0.2 µl/min overnight. The flow rate was increased to 1.5 µl/min the next morning and, after a 1 hour equilibration period, the final dose of morphine was administered and sample collection began and dialysates were collected manually every 20 minutes and immediately placed in −80° C. until analysis. In one set of animals opioid withdrawal was precipitated with 10 mg/kg naloxone subcutaneously (dose volume 1 ml/mg) naloxone 60 minutes after the morphine administration. Collection tubes were pre-filled with 3 µl of 0.02% EDTA (anti-oxidant) in 1% ethanol. After collection of three baseline samples, morphine or vehicle was administered in the same manner as described above. Dialysates were analyzed by HPLC within 2 weeks of collection.

Dopamine in the dialysates was determined using an ESA 5600A COULARRAY detector with an ESA 5014B analytical cell and an ESA 5020 guard cell connected to an ESA HR80 column (C18, 3 1m, 80×3 mm) which was maintained at 30° C. The mobile phase was 150 mM sodium dihydrogen phosphate monohydrate, 4.76 mM citric acid monohydrate, 3 mM sodium dodecyl sulfate, 50 µM EDTA, 10% methanol, and 15% acetonitrile, pH=5.6 with sodium hydroxide. The potentials were set at −75 and +220 mV, and the guard cell potential was set at +250 mV. Injections were performed with an ESA 542 autosampler using an injection volume of 27 µl. Quantitative comparisons were made with external standards (Sigma-Aldrich, St Louis, Mo.) that were run each day.

To verify probe placement, rats were euthanized with 65 mg/kg ip sodium pentobarbital. The brains were removed, frozen in chilled isopentane, and cryostat sectioned (40 µm) at −20° C. Sections were mounted on gelatin-treated slides, stained with cresyl violet, and coverslipped. Only rats with probes placed within the nucleus accumbens were included in the analysis.

Results

Figure 10:
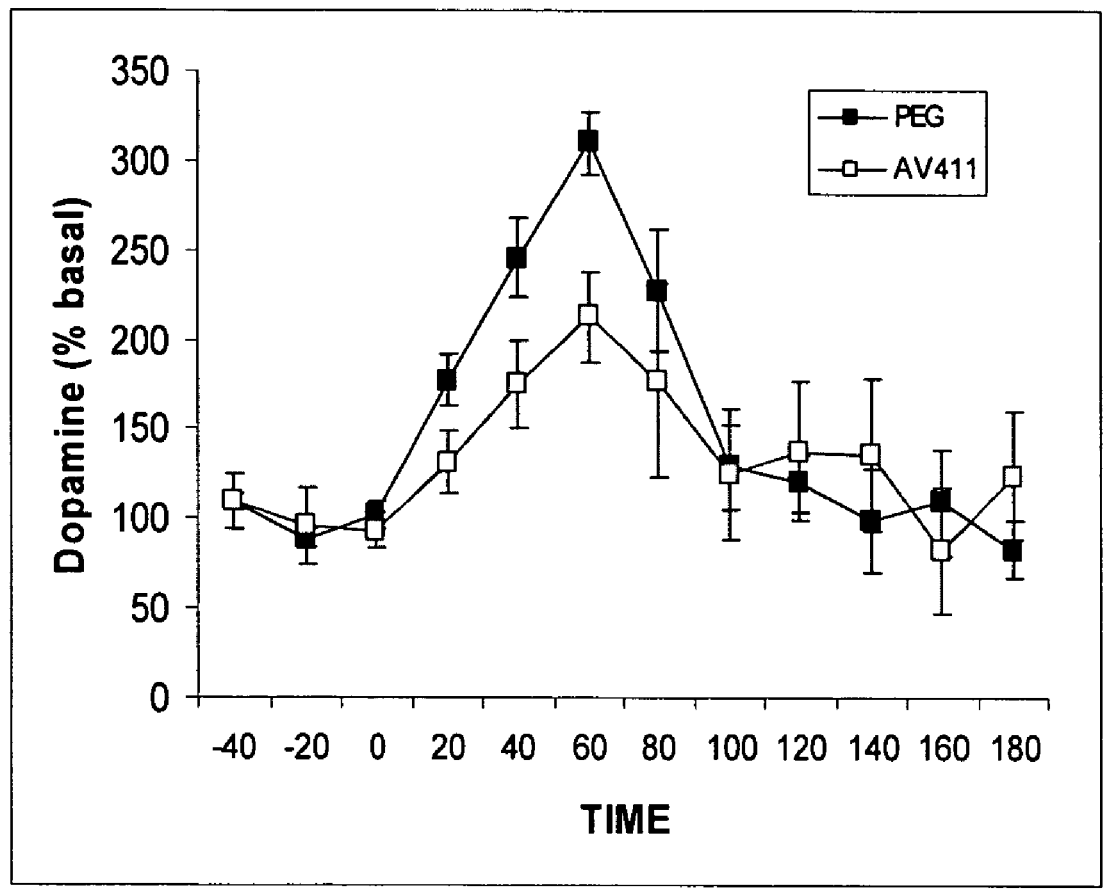
FIG. 10 shows nucleus accumbens dopamine levels in morphine-dependent animals following morphine administration (at time 0) and during naloxone precipitated opioid withdrawal (10 mg/kg of naloxone was administered subcutaneously for 60 minutes) in animals treated with ibudilast (7.5 mg/kg) or vehicle (PEG).
Figure 11:
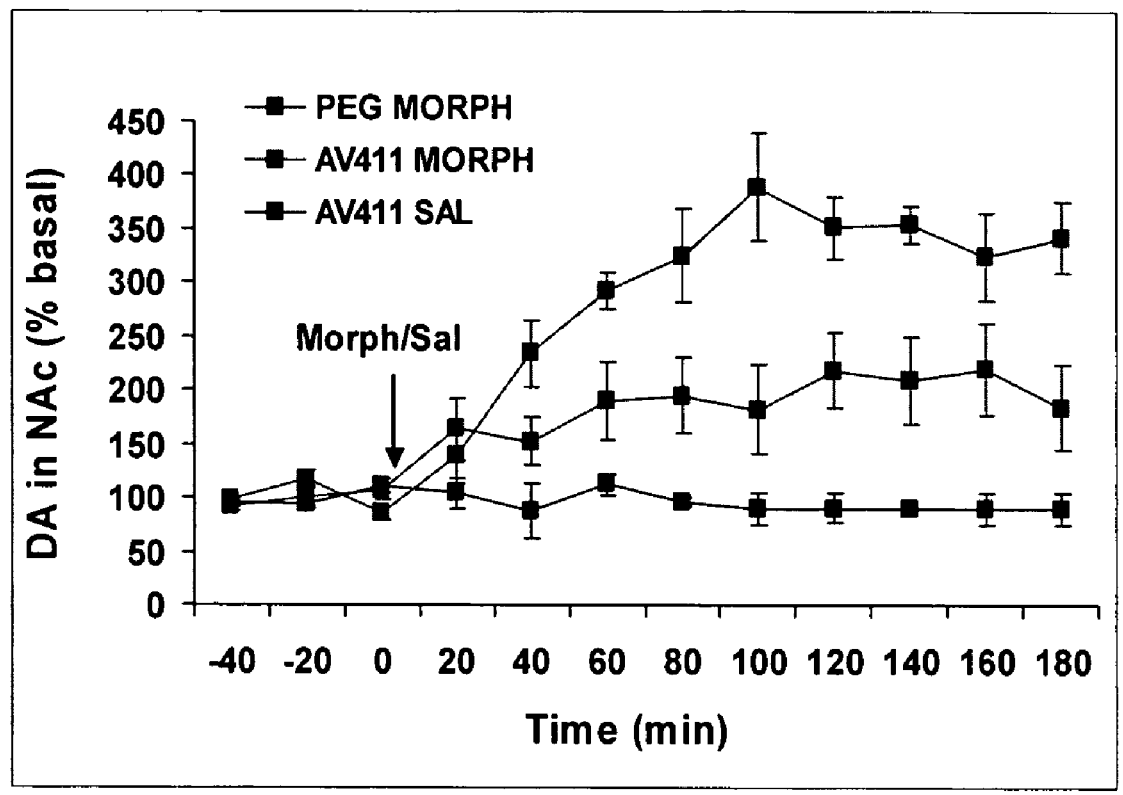
FIG. 11 shows nucleus accumbens dopamine levels in morphine-dependent animals following morphine administration (at time 0) in animals treated with ibudilast (7.5 mg/kg), morphine, or a combination of ibudilast and morphine.

Treatment with ibudilast resulted in dramatically reduced morphine induced nucleus accumbens dopamine increases in morphine-dependent animals during morphine administration and during naloxone precipitated opioid withdrawal or spontaneous opioid withdrawal (FIGS. 10 and 11). FIG. 10 shows ibudilast reduced nucleus accumbens dopamine levels in morphine-dependent animals during naloxone precipitated opioid withdrawal (10 mg/kg of naloxone was administered subcutaneously for 60 minutes) in animals treated with 7.5 mg/kg ibudilast. FIG. 11 shows that ibudilast also reduced nucleus accumbens dopamine levels in morphine-dependent animals following morphine administration (at time 0) during spontaneous opioid withdrawal in animals treated with ibudilast (7.5 mg/kg) or a combination of ibudilast and morphine.

CONCLUSIONS

Ibudilast treatment was shown to significantly reduce the increased dopamine levels observed in the brain nucleus accumbens following morphine treatment in a rat model of morphine dependence. Since drugs of abuse cause increased dopamine in the nucleus accumbens (and this increase is what is thought to mediate the "reward" associated with such drugs), the results imply that ibudilast therapy may similarly reduce dependence and attenuate withdrawal for any addictive disorder. Hence, ibudilast treatment is indicated for not only syndromes associated with opiates, but also for other classes of drugs, such as psychostimulants (cocaine, amphetamine, methamphetamine), cannabinoids, and alcohol. Furthermore, ibudilast treatment could also be extended to potentially attenuate "behavioral addictions" such as gambling and over-eating.

Although preferred embodiments of the subject invention have been described in some detail, it is understood that obvious variations can be made without departing from the spirit and the scope of the invention as claimed herein.

All references cited herein, including patents, patent applications and other publications, are hereby incorporated by reference in their entireties.

What is claimed is:

1. A method for suppressing the release of dopamine in the nucleus accumbens of a subject suffering from a drug addiction or drug dependence comprising administering to the subject an effective amount of ibudilast.

2. The method of claim 1, wherein the drug addiction or dependence is an opioid addiction or dependence to one or more opioids selected from the group consisting of morphine, methadone, buprenorphine, levomethadyl acetate, L-α-acetylmethadol, fentanyl, alfentanyl, alphaprodine, anileridine, bezitramide, codeine, dihydrocodeine, diphenoxylate, ethylmorphine, heroin, hydrocodone, hydromorphone, isomethadone, levomethorphan, levorphanol, metazocine, metopon, opium extracts, opium fluid extracts, powdered opium, granulated opium, raw opium, tincture of opium, oxycodone, oxymorphone, pethidine, phenazocine, piminodine, racemethorphan, racemorphan and thebaine.

3. The method of claim 1, wherein the subject is human.

4. The method of claim 1, wherein the ibudilast is administered systemically.

5. The method of claim 4, wherein the ibudilast is administered intravenously, subcutaneously, orally, intranasally, or sublingually.

6. The method of claim 1, wherein the ibudilast is administered centrally.

7. The method of claim 6, wherein the ibudilast is administered intrathecally.

8. The method of claim 1, wherein multiple therapeutically effective doses of ibudilast are administered to the subject.

9. The method of claim 8, wherein ibudilast is administered according to a daily dosing regimen.

10. The method of claim 9, wherein ibudilast is administered twice a day.

11. The method of claim 8, wherein ibudilast is administered intermittently.

12. A method for treating a drug addiction or drug dependence comprising administering to a subject in need thereof a therapeutically effective amount of ibudilast.

13. The method of claim 12, wherein the drug addiction or dependence is an opioid addiction or dependence to one or more opioids selected from the group consisting of morphine, methadone, fentanyl, alfentanyl, alphaprodine, anileridine, bezitramide, codeine, dihydrocodeine, diphenoxylate, ethylmorphine, heroin, hydrocodone, hydromorphone, isomethadone, levomethorphan, levorphanol, metazocine, metopon, opium extracts, opium fluid extracts, powdered opium, granulated opium, raw opium, tincture of opium, oxycodone oxymorphone, pethidine, phenazocine, piminodine, racemethorphan, racemorphan and thebaine.

14. The method of claim 12, wherein ibudilast diminishes or eliminates addiction-related or dependence-related behavior of the subject.

15. The method of claim 12, wherein ibudilast diminishes or eliminates cravings associated with addiction to one or more drugs in the subject.

16. The method of claim 12, wherein ibudilast diminishes or eliminates incentive salience of drug- or addictive behavior-associated cues in the subject.

17. The method of claim 12, wherein ibudilast diminishes or eliminates symptoms of withdrawal syndrome in the subject.

18. The method of claim 12, wherein ibudilast diminishes or eliminates weight loss related to withdrawal syndrome in the subject.

19. The method of claim 12, wherein ibudilast diminishes or eliminates glial cell activation in the subject.

20. The method of claim 19, wherein ibudilast diminishes or eliminates astrocyte or microglia activation in the subject.

21. The method of claim 12, wherein ibudilast diminishes or eliminates drug-induced increases in interleukin-1 expression in the subject.

22. The method of claim 12, wherein the subject is human.

23. The method of claim 12, wherein the ibudilast is administered systemically.

24. The method of claim 23, wherein the ibudilast is administered intravenously, subcutaneously, orally, intranasally, or sublingually.

25. The method of claim 12, wherein the ibudilast is administered centrally.

26. The method of claim 25, wherein the ibudilast is administered intrathecally.

27. The method of claim 12, wherein multiple therapeutically effective doses of ibudilast are administered to the subject.

28. The method of claim 27, wherein ibudilast is administered according to a daily dosing regimen.

29. The method of claim 28, wherein ibudilast is administered twice a day.

30. The method of claim 27, wherein ibudilast is administered intermittently.

31. The method of claim 12, further comprising administering one or more agents other than ibudilast for treating an addiction or dependence.

32. The method of claim 31, wherein one or more agents are selected from the group consisting of analgesics, NSAIDs, antiemetics, antidiarrheals, alpha -2-antagonists, benzodiazepines, anticonvulsants, antidepressants and insomnia therapeutics.

33. The method of claim 32, wherein one or more agents are selected from the group consisting of buprenorphine, naloxone, methadone, levomethadyl acetate, L-alpha acetylmethadol (LAAM), hydroxyzine, diphenoxylate, atropine, chlordiazepoxide, carbamazepine, mianserin, benzodiazepine, phenoziazine, disulfiram, acamprosate, topiramate, ondansetron, sertraline, bupropion, amantadine, amiloride, isradipine, tiagabine, baclofen, propranolol, desipramine, carbamazepine, valproate, lamotrigine, doxepin, fluoxetine, imipramine, moclobemide, nortriptyline, paroxetine, sertraline, tryptophan, venlafaxine, trazodone, quetiapine, zolpidem, zopiclone, zaleplon, gabapentin, naltrexone, paracetamol, metoclopramide, loperamide, clonidine, lofexidine and diazepam.

34. A method of treating an opioid withdrawal syndrome in a mammalian subject comprising administering one or more doses of ibudilast.

35. The method of claim 34, wherein the subject is human.

36. The method of claim 34, wherein the opioid withdrawal syndrome is caused by reduction or cessation of administration of an opioid in the subject.

37. The method of claim 36, wherein the opioid is selected from the group consisting of morphine, methadone and fentanyl.

38. The method of claim 37, wherein the opioid is morphine.

39. The method of claim 34, wherein the ibudilast is administered systemically.

40. The method of claim 39, wherein the ibudilast is administered intravenously, subcutaneously, orally, intranasally, or sublingually.

41. The method of claim 34, wherein the ibudilast is administered centrally.

42. The method of claim 41, wherein the ibudilast is administered intrathecally.

43. The method of claim 34, wherein multiple therapeutically effective doses of ibudilast are administered to the subject.

44. The method of claim 43, wherein ibudilast is administered according to a daily dosing regimen.

45. The method of claim 44, wherein ibudilast is administered twice a day.

46. The method of claim 34, wherein ibudilast is administered intermittently.

47. The method of claim 34, further comprising administering one or more agents other than ibudilast for treatment of opioid withdrawal.

48. The method of claim 47, wherein one or more agents are selected from the group consisting of analgesics, NSAIDs, antiemetics, antidiarrheals, alpha -2-antagonists and benzodiazepines.

49. The method of claim 48, wherein one or more agents are selected from the group consisting of naltrexone, paracetamol, metoclopramide, loperamide, clonidine, lofexidine and diazepam.

50. The method of claim 34, wherein ibudilast diminishes or eliminates weight loss related to withdrawal syndrome in the subject.

51. The method of claim 34, wherein ibudilast diminishes or eliminates glial cell activation in the subject.

52. The method of claim 34, wherein ibudilast diminishes or eliminates astrocyte or microglia activation in the subject.

53. The method of claim 34, wherein ibudilast diminishes or eliminates drug-induced increases in interleukin-1 expression in the subject.

* * * * *